(12) United States Patent
Chen et al.

(10) Patent No.: US 9,701,691 B2
(45) Date of Patent: Jul. 11, 2017

(54) THIENOPYRIMIDINE COMPOUNDS

(71) Applicant: Hoffmann-La Roche Inc., Nutley, NJ (US)

(72) Inventors: Shaoqing Chen, Bridgewater, NJ (US); Johannes Cornelius Hermann, Jersey City, NJ (US); Nam T. Le, Verona, NJ (US); Matthew C. Lucas, Lexington, MA (US); Fernando Padilla, Verona, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 80 days.

(21) Appl. No.: 13/738,103

(22) Filed: Jan. 10, 2013

(65) Prior Publication Data

US 2013/0178460 A1    Jul. 11, 2013

Related U.S. Application Data

(60) Provisional application No. 61/584,863, filed on Jan. 10, 2012.

(51) Int. Cl.
| | |
|---|---|
| C07D 495/04 | (2006.01) |
| C07D 519/00 | (2006.01) |
| A61K 45/06 | (2006.01) |
| A61K 31/519 | (2006.01) |
| C07D 513/04 | (2006.01) |

(52) U.S. Cl.
CPC .......... C07D 495/04 (2013.01); A61K 31/519 (2013.01); A61K 45/06 (2013.01); C07D 513/04 (2013.01); C07D 519/00 (2013.01)

(58) Field of Classification Search
CPC ........................... C07D 495/04; A61K 31/519
USPC ....................................... 544/278; 514/260.1
See application file for complete search history.

(56) References Cited

U.S. PATENT DOCUMENTS

2014/0303149 A1*  10/2014  Arora et al. .............. 514/217.06

FOREIGN PATENT DOCUMENTS

| | | |
|---|---|---|
| EP | 1329454 | 7/2003 |
| EP | 1731523 | 12/2006 |
| WO | 9924440 | 5/1999 |
| WO | 2008/059368 | 5/2008 |
| WO | 2009037468 | 3/2009 |
| WO | 2009062258 | 5/2009 |
| WO | 2011/049332 | 4/2011 |
| WO | 2011/062372 | 5/2011 |
| WO | 2011093672 | 8/2011 |
| WO | 2012/007375 | 1/2012 |

OTHER PUBLICATIONS

International Search Report, PCT/EP2013/050139, dated Feb. 22, 2013.
Ruzza et al., Expert Opinion Therapeutic Patents 19(10):1361-1376 ( 2009).
The English translation of Chinese Office Action, issued on Jul. 7, 2015, in the related Chinese patent application No. 201380013256.X.
The English translation of the Japanese Office Action, issued on Jul. 12, 2016, in the related Japanese patent application No. 2014-550712.

\* cited by examiner

*Primary Examiner* — Susanna Moore

(57) ABSTRACT

The present invention relates to the use of novel compounds of Formula I:

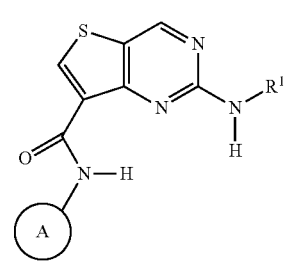

wherein all variable substituents are defined as described herein, which are SYK inhibitors and are useful for the treatment of auto-immune and inflammatory diseases.

6 Claims, No Drawings

THIENOPYRIMIDINE COMPOUNDS

PRIORITY TO RELATED APPLICATIONS

This application is entitled to the benefit of U.S. provisional patent application Ser. No. 61/584,863 filed on Jan. 10, 2012.

FIELD OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphoryated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FceRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FceR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of autoimmune and inflammatory diseases by targeting the SYK pathway or by inhibition of SYK kinase.

SUMMARY OF THE INVENTION

The application provides a compound of Formula I

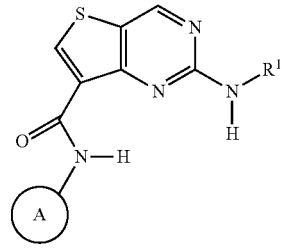

wherein:
  each A is independently monocyclic or bicyclic aryl or heteroaryl, optionally substituted with one or more A';
  each A' is independently lower alkyl, halo, cyano, or heteroaryl;
  each $R^1$ is independently lower alkyl, cycloalkyl or heterocycloalkyl optionally substituted with one or more $R^{1'}$; and
  each $R^{1'}$ is independently amino or lower alkyl amino;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds. The symbols "*" at the end of a bond or "------" drawn through a bond each refer to the point of attachment of a functional group or other chemical moiety to the rest of the molecule of which it is a part. Thus, for example:

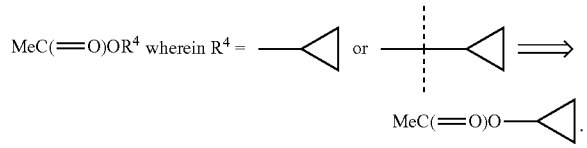

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—D—C(—OH)=CH—), amide/imidic acid (—C(=O)—NH—D—C(—OH)=N—) and amidine (—C(=NR)—NH—D—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK

The application provides a compound of Formula I

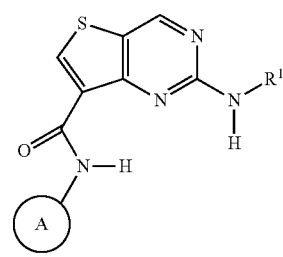

wherein:
  each A is independently monocyclic or bicyclic aryl or heteroaryl, optionally substituted with one or more A';
  each A' is independently lower alkyl, halo, cyano, or heteroaryl;

each $R^1$ is independently lower alkyl, cycloalkyl or heterocycloalkyl optionally substituted with one or more $R^{1'}$; and each $R^{1'}$ is independently amino or lower alkyl amino; or a pharmaceutically acceptable salt thereof.

The application provides a compound of Formula I, wherein $R^1$ is cyclohexyl substituted with amino.

The application provides a compound of Formula I, wherein $R^1$ is tetrahydro pyranyl substituted with amino.

The application provides a compound of Formula I, wherein A is pyridyl, optionally substituted with one or more A'.

The application provides a compound of Formula I, wherein $R^1$ is cyclohexyl substituted with amino and A is pyridyl, optionally substituted with one or more A'.

The application provides a compound of Formula I, wherein $R^1$ is tetrahydro pyranyl substituted with amino and A is pyridyl, optionally substituted with one or more A'.

The application provides a compound of Formula I, wherein A is bicyclic heteroaryl, optionally substituted with one or more A'.

The application provides a compound of Formula I, wherein $R^1$ is cyclohexyl substituted with amino and A is bicyclic heteroaryl, optionally substituted with one or more A'.

The application provides a compound of Formula I, wherein $R^1$ is tetrahydro pyranyl substituted with amino and A is bicyclic heteroaryl, optionally substituted with one or more A'.

The application provides a compound of Formula I, wherein A is heteroaryl, optionally substituted with one or more A'.

The application provides a compound of Formula I, wherein $R^1$ is cyclohexyl substituted with amino and A is heteroaryl, optionally substituted with one or more A'.

The application provides a compound of Formula I, wherein $R^1$ is tetrahydro pyranyl substituted with amino and A is heteroaryl, optionally substituted with one or more A'.

The application provides a compound of Formula I, wherein $R^1$ is lower alkyl substituted with amino or lower alkyl amino.

The application provides a compound of Formula I, wherein $R^1$ is heterocycloalkyl.

The application provides a compound of Formula I, wherein $R^1$ is lower alkyl substituted with amino or lower alkyl amino and A is bicyclic heteroaryl, optionally substituted with one or more A'.

The application provides a compound of Formula I, wherein $R^1$ is heterocycloalkyl and A is bicyclic heteroaryl, optionally substituted with one or more A'.

The application provides a compound of Formula I, wherein $R^1$ is lower alkyl substituted with amino or lower alkyl amino and A is heteroaryl, optionally substituted with one or more A'.

The application provides a compound of Formula I, wherein $R^1$ is heterocycloalkyl and A is heteroaryl, optionally substituted with one or more A'.

The application provides a compound of Formula I, wherein $R^1$ is lower alkyl substituted with amino or lower alkyl amino and A is pyridyl, optionally substituted with one or more A'.

The application provides a compound of Formula I, wherein $R^1$ is heterocycloalkyl and A is pyridyl, optionally substituted with one or more A'.

The application provides a compound of Formula I, selected from the group consisting of:

2-((3R,4R)-3-Amino-tetrahydro-pyran-4-ylamino)-thieno[3,2-d]pyrimidine-7-carboxylic acid (6-ethyl-pyridin-2-yl)-amide;

2-((1R,2S)-2-Amino-cyclohexylamino)-thieno[3,2-d]pyrimidine-7-carboxylic acid (8-methyl-quinolin-6-yl)-amide;

2-((1R,2S)-2-Amino-cyclohexylamino)-thieno[3,2-d]pyrimidine-7-carboxylic acid (8-ethyl-quinolin-6-yl)-amide;

2-((1R,2S)-2-Amino-cyclohexylamino)-thieno[3,2-d]pyrimidine-7-carboxylic acid (5-cyano-6-methyl-pyridin-2-yl)-amide;

2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide;

2-((3R,4R)-3-Amino-tetrahydro-pyran-4-ylamino)-thieno[3,2-d]pyrimidine-7-carboxylic acid (6-[1,2,3]triazol-1-yl-pyridin-2-yl)-amide;

2-((1R,2S)-2-Amino-cyclohexylamino)-thieno[3,2-d]pyrimidine-7-carboxylic acid [1,6]naphthyridin-2-ylamide;

2-((1R,2S)-2-Amino-cyclohexylamino)-thieno[3,2-d]pyrimidine-7-carboxylic acid benzothiazol-2-ylamide;

2-((1R,2S)-2-Amino-cyclohexylamino)-thieno[3,2-d]pyrimidine-7-carboxylic acid (1H-benzoimidazol-2-yl)-amide;

2-((1R,2S)-2-Amino-cyclohexylamino)-thieno[3,2-d]pyrimidine-7-carboxylic acid [1,5]naphthyridin-2-ylamide;

2-((3R,4R)-3-Amino-tetrahydro-pyran-4-ylamino)-thieno[3,2-d]pyrimidine-7-carboxylic acid (1-methyl-1H-benzoimidazol-4-yl)-amide hydrochloride;

2-(2-Amino-ethylamino)-thieno[3,2-d]pyrimidine-7-carboxylic acid (1-methyl-1H-benzoimidazol-4-yl)-amide; compound with trifluoro-acetic acid;

2-(Azetidin-3-ylamino)-thieno[3,2-d]pyrimidine-7-carboxylic acid (1-methyl-1H-benzoimidazol-4-yl)-amide hydrochloride;

2-(2-Methylamino-ethylamino)-thieno[3,2-d]pyrimidine-7-carboxylic acid (1-methyl-1H-benzoimidazol-4-yl)-amide hydrochloride salt;

2-((1R,2S)-2-Amino-cyclohexylamino)-thieno[3,2-d]pyrimidine-7-carboxylic acid (6-fluoro-1-methyl-1H-indazol-3-yl)-amide; compound with trifluoro-acetic acid;

2-((3R,4R)-3-Amino-tetrahydro-pyran-4-ylamino)-thieno[3,2-d]pyrimidine-7-carboxylic acid naphthalen-2-ylamide;

2-((3R,4R)-3-Amino-tetrahydro-pyran-4-ylamino)-thieno[3,2-d]pyrimidine-7-carboxylic acid (5-methyl-pyridin-2-yl)-amide;

2-((3R,4R)-3-Amino-tetrahydro-pyran-4-ylamino)-thieno[3,2-d]pyrimidine-7-carboxylic acid p-tolylamide;

2-((3R,4R)-3-Amino-tetrahydro-pyran-4-ylamino)-thieno[3,2-d]pyrimidine-7-carboxylic acid (1-methyl-1H-pyrazol-3-yl)-amide;

2-((3R,4R)-3-Amino-tetrahydro-pyran-4-ylamino)-thieno[3,2-d]pyrimidine-7-carboxylic acid thiazolo[4,5-b]pyridin-2-ylamide;

2-((3R,4R)-3-Amino-tetrahydro-pyran-4-ylamino)-thieno[3,2-d]pyrimidine-7-carboxylic acid (1-methyl-1H-pyrazol-4-yl)-amide;

2-((3R,4R)-3-Amino-tetrahydro-pyran-4-ylamino)-thieno[3,2-d]pyrimidine-7-carboxylic acid pyrazolo[1,5-a]pyrimidin-3-ylamide;

2-((3R,4R)-3-Amino-tetrahydro-pyran-4-ylamino)-thieno[3,2-d]pyrimidine-7-carboxylic acid imidazo[1,2-b]pyridazin-3-ylamide;

2-((3R,4R)-3-Amino-tetrahydro-pyran-4-ylamino)-thieno
[3,2-d]pyrimidine-7-carboxylic acid (4,6-dimethyl-pyridin-2-yl)-amide; and
2-((3R,4R)-3-Amino-tetrahydro-pyran-4-ylamino)-thieno
[3,2-d]pyrimidine-7-carboxylic acid (5,6-dimethyl-pyridin-2-yl)-amide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

A compound, method, or composition as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of triazolopyridine compounds according to generic Formula I.

TABLE I

| Compound | Nomenclature | Structure |
| --- | --- | --- |
| 1 | 2-((3R,4R)-3-Amino-tetrahydro-pyran-4-ylamino)-thieno[3,2-d]pyrimidine-7-carboxylic acid (6-ethyl-pyridin-2-yl)-amide | 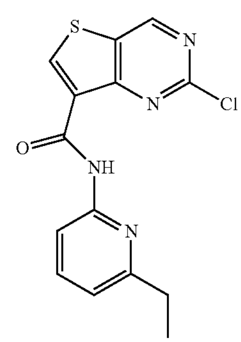 [SMILES: CCc1cccc(NC(=O)c2csc3cnc(Cl)nc23)n1] |

TABLE I-continued

| Compound | Nomenclature | Structure |
|---|---|---|
| 2 | 2-((1R,2S)-2-Amino-cyclohexylamino)-thieno[3,2-d]pyrimidine-7-carboxylic acid (8-methyl-quinolin-6-yl)-amide | 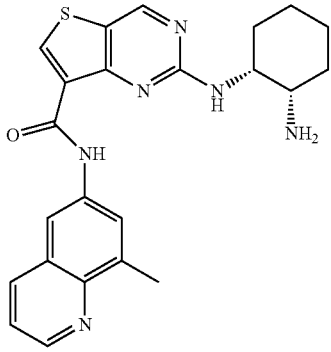 [SMILES: Cc1cc(NC(=O)c2csc3cnc(N[C@@H]4CCCC[C@@H]4N)nc23)cc2cccnc12] |
| 3 | 2-((1R,2S)-2-Amino-cyclohexylamino)-thieno[3,2-d]pyrimidine-7-carboxylic acid (8-ethyl-quinolin-6-yl)-amide | 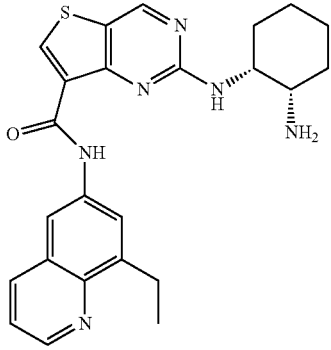 [SMILES: CCc1cc(NC(=O)c2csc3cnc(N[C@@H]4CCCC[C@@H]4N)nc23)cc2cccnc12] |
| 4 | 2-((1R,2S)-2-Amino-cyclohexylamino)-thieno[3,2-d]pyrimidine-7-carboxylic acid (5-cyano-6-methyl-pyridin-2-yl)-amide | 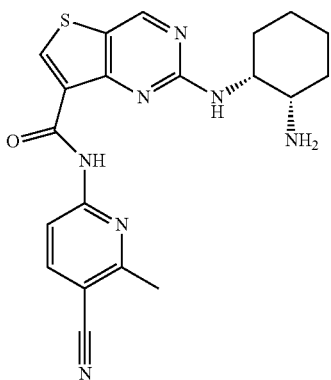 [SMILES: Cc1nc(NC(=O)c2csc3cnc(N[C@@H]4CCCC[C@@H]4N)nc23)ccc1C#N] |
| 5 | 2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide | 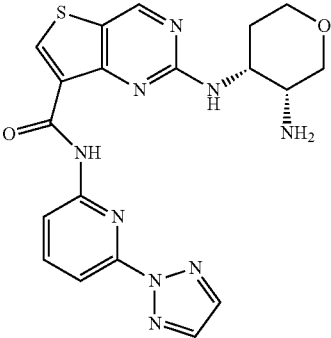 [SMILES: N[C@H]1COCC[C@H]1Nc1ncc2scc(C(=O)Nc3cccc(-n4nccn4)n3)c2n1] |

TABLE I-continued

| Compound | Nomenclature | Structure |
|---|---|---|
| 6 | 2-((3R,4R)-3-Amino-tetrahydro-pyran-4-ylamino)-thieno[3,2-d]pyrimidine-7-carboxylic acid (6-[1,2,3]triazol-1-yl-pyridin-2-yl)-amide | 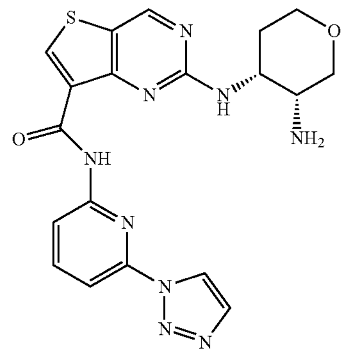 [SMILES: N[C@H]1COCC[C@H]1Nc1ncc2scc(C(=O)Nc3cccc(-n4ccnn4)n3)c2n1] |
| 7 | 2-((1R,2S)-2-Amino-cyclohexylamino)-thieno[3,2-d]pyrimidine-7-carboxylic acid [1,6]naphthyridin-2-ylamide | 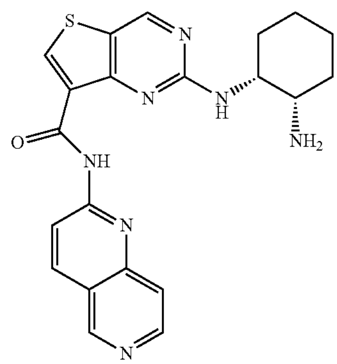 [SMILES: N[C@H]1CCCC[C@H]1Nc1ncc2scc(C(=O)Nc3ccc4cnccc4n3)c2n1] |
| 8 | 2-((1R,2S)-2-Amino-cyclohexylamino)-thieno[3,2-d]pyrimidine-7-carboxylic acid benzothiazol-2-ylamide | 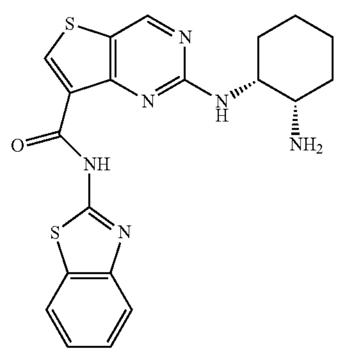 [SMILES: N[C@H]1CCCC[C@H]1Nc1ncc2scc(C(=O)Nc3nc4ccccc4s3)c2n1] |
| 9 | 2-((1R,2S)-2-Amino-cyclohexylamino)-thieno[3,2-d]pyrimidine-7-carboxylic acid (1H-benzoimidazol-2-yl)-amide | 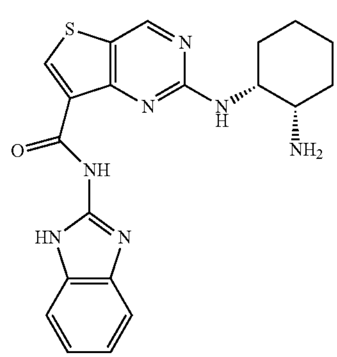 [SMILES: N[C@H]1CCCC[C@H]1Nc1ncc2scc(C(=O)Nc3nc4ccccc4[nH]3)c2n1] |

TABLE I-continued

| Compound | Nomenclature | Structure |
|---|---|---|
| 10 | 2-((1R,2S)-2-Amino-cyclohexylamino)-thieno[3,2-d]pyrimidine-7-carboxylic acid [1,5]naphthyridin-2-ylamide | 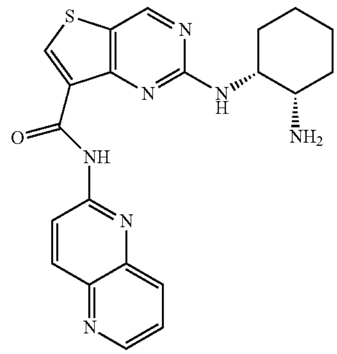 [SMILES: N[C@H]1CCCC[C@H]1Nc1ncc2scc(C(=O)Nc3ccc4ncccc4n3)c2n1] |
| 11 | 2-((3R,4R)-3-Amino-tetrahydro-pyran-4-ylamino)-thieno[3,2-d]pyrimidine-7-carboxylic acid (1-methyl-1H-benzoimidazol-4-yl)-amide hydrochloride | 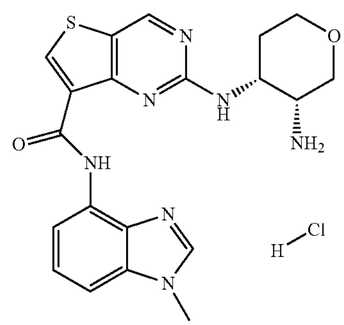 [SMILES: Cn1cnc2c(NC(=O)c3csc4cnc(N[C@@H]5CCOC[C@@H]5N)nc34)cccc21 ; Cl] |
| 12 | 2-(2-Amino-ethylamino)-thieno[3,2-d]pyrimidine-7-carboxylic acid (1-methyl-1H-benzoimidazol-4-yl)-amide trifluoroacetate | 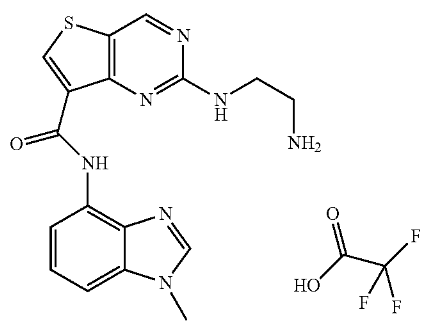 [SMILES: Cn1cnc2c(NC(=O)c3csc4cnc(NCCN)nc34)cccc21 ; O=C(O)C(F)(F)F] |
| 13 | 2-(Azetidin-3-ylamino)-thieno[3,2-d]pyrimidine-7-carboxylic acid (1-methyl-1H-benzoimidazol-4-yl)-amide hydrochloride | 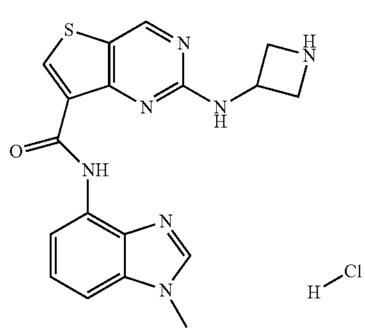 [SMILES: Cn1cnc2c(NC(=O)c3csc4cnc(NC5CNC5)nc34)cccc21 ; Cl] |

TABLE I-continued

| Compound | Nomenclature | Structure |
|---|---|---|
| 14 | 2-(2-Methylamino-ethylamino)-thieno[3,2-d]pyrimidine-7-carboxylic acid (1-methyl-1H-benzoimidazol-4-yl)-amide hydrochloride | 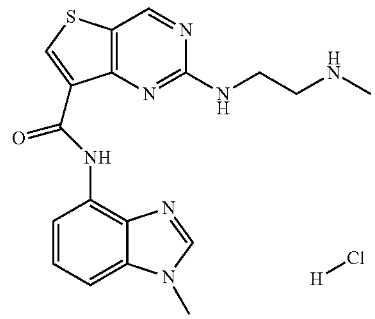 [SMILES: CNCCNc1ncc2scc(C(=O)Nc3cccc4c3ncn4C)c2n1 ; Cl] |
| 15 | 2-((1R,2S)-2-Amino-cyclohexylamino)-thieno[3,2-d]pyrimidine-7-carboxylic acid (6-fluoro-1-methyl-1H-indazol-3-yl)-amide trifluoroacetate | 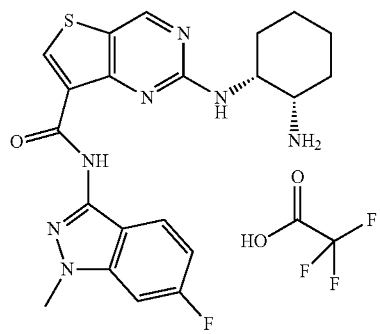 |
| 16 | 2-((3R,4R)-3-Amino-tetrahydro-pyran-4-ylamino)-thieno[3,2-d]pyrimidine-7-carboxylic acid naphthalen-2-ylamide | 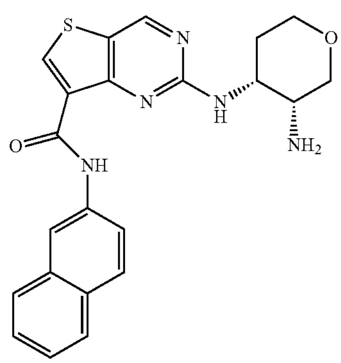 [SMILES: N[C@H]1COCC[C@H]1Nc1ncc2scc(C(=O)Nc3ccc4ccccc4c3)c2n1] |
| 17 | 2-((3R,4R)-3-Amino-tetrahydro-pyran-4-ylamino)-thieno[3,2-d]pyrimidine-7-carboxylic acid (5-methyl-pyridin-2-yl)-amide | 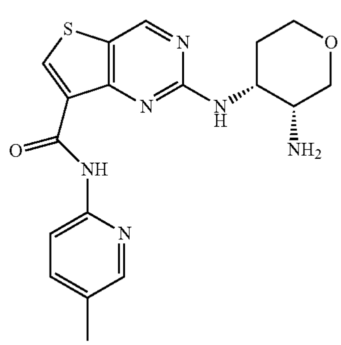 [SMILES: Cc1ccc(NC(=O)c2csc3cnc(N[C@@H]4CCOC[C@@H]4N)nc23)nc1] |

TABLE I-continued

| Compound | Nomenclature | Structure |
|---|---|---|
| 18 | 2-((3R,4R)-3-Amino-tetrahydro-pyran-4-ylamino)-thieno[3,2-d]pyrimidine-7-carboxylic acid p-tolylamide | 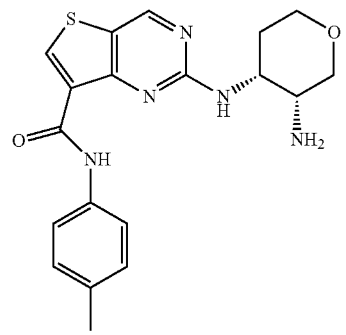 [SMILES: Cc1ccc(NC(=O)c2csc3cnc(N[C@@H]4CCOC[C@@H]4N)nc23)cc1] |
| 19 | 2-((3R,4R)-3-Amino-tetrahydro-pyran-4-ylamino)-thieno[3,2-d]pyrimidine-7-carboxylic acid (1-methyl-1H-pyrazol-3-yl)-amide | 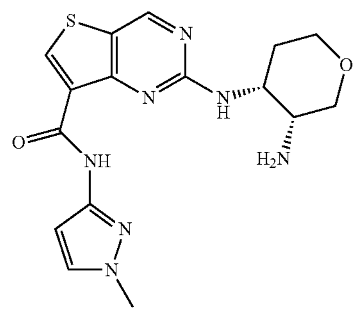 [SMILES: Cn1ccc(NC(=O)c2csc3cnc(N[C@@H]4CCOC[C@@H]4N)nc23)n1] |
| 20 | 2-((3R,4R)-3-Amino-tetrahydro-pyran-4-ylamino)-thieno[3,2-d]pyrimidine-7-carboxylic acid thiazolo[4,5-b]pyridin-2-ylamide | 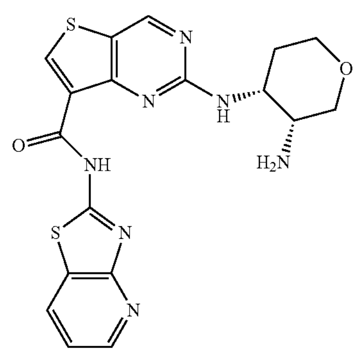 [SMILES: N[C@H]1COCC[C@H]1Nc1ncc2scc(C(=O)Nc3nc4ncccc4s3)c2n1] |
| 21 | 2-((3R,4R)-3-Amino-tetrahydro-pyran-4-ylamino)-thieno[3,2-d]pyrimidine-7-carboxylic acid (1-methyl-1H-pyrazol-4-yl)-amide | 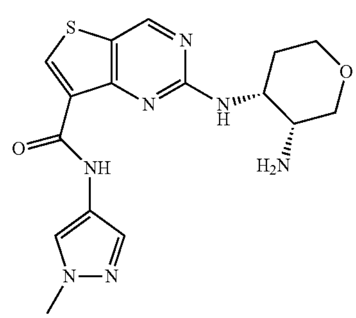 [SMILES: Cn1cc(NC(=O)c2csc3cnc(N[C@@H]4CCOC[C@@H]4N)nc23)cn1] |
| 22 | 2-((3R,4R)-3-Amino-tetrahydro-pyran-4-ylamino)-thieno[3,2-d]pyrimidine-7-carboxylic acid pyrazolo[1,5-a]pyrimidin-3-ylamide | 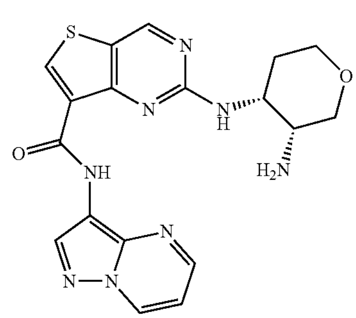 [SMILES: N[C@H]1COCC[C@H]1Nc1ncc2scc(C(=O)Nc3cnn4cccnc34)c2n1] |

TABLE I-continued

| Compound | Nomenclature | Structure |
|---|---|---|
| 23 | 2-((3R,4R)-3-Amino-tetrahydro-pyran-4-ylamino)-thieno[3,2-d]pyrimidine-7-carboxylic acid imidazo[1,2-b]pyridazin-3-ylamide | 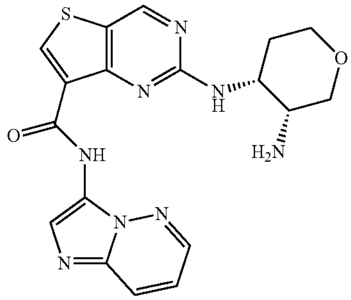 [SMILES: N[C@H]1COCC[C@H]1Nc1ncc2scc(C(=O)Nc3cnc4cccnn34)c2n1] |
| 24 | 2-((3R,4R)-3-Amino-tetrahydro-pyran-4-ylamino)-thieno[3,2-d]pyrimidine-7-carboxylic acid (4,6-dimethyl-pyridin-2-yl)-amide | 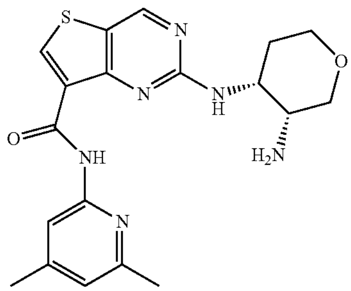 [SMILES: Cc1cc(C)nc(NC(=O)c2csc3cnc(N[C@@H]4CCOC[C@@H]4N)nc23)c1] |
| 25 | 2-((3R,4R)-3-Amino-tetrahydro-pyran-4-ylamino)-thieno[3,2-d]pyrimidine-7-carboxylic acid (5,6-dimethyl-pyridin-2-yl)-amide | 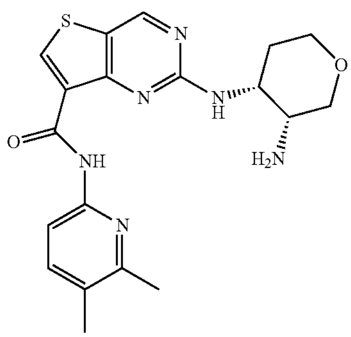 [SMILES: Cc1ccc(NC(=O)c2csc3cnc(N[C@@H]4CCOC[C@@H]4N)nc23)nc1C] |

Synthesis
General Schemes

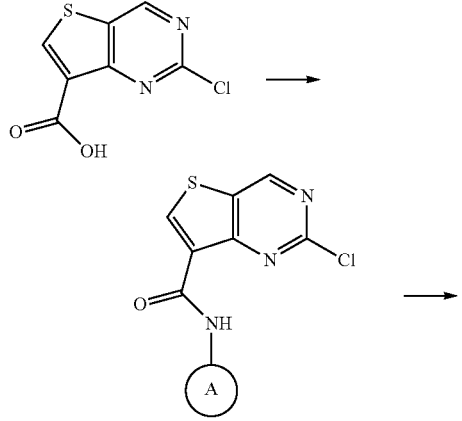

General Scheme 1

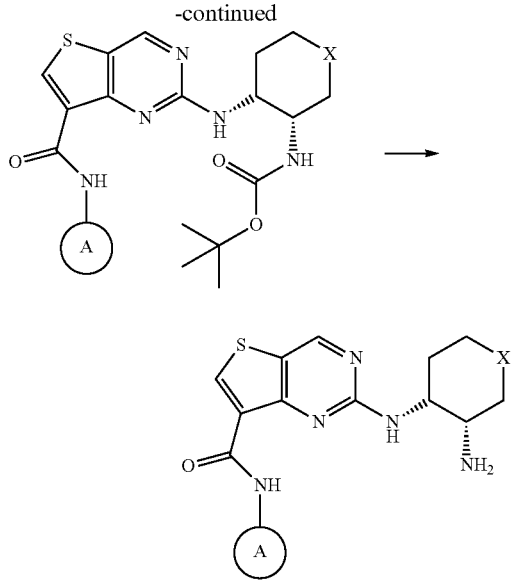

General Scheme 2

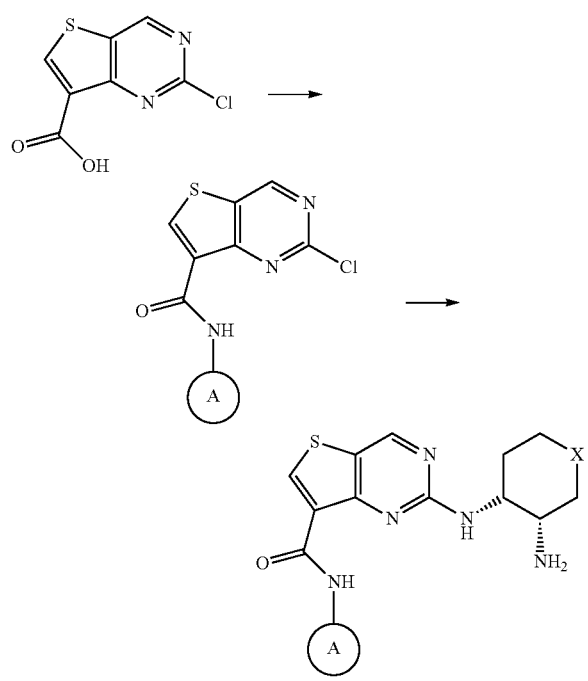

In the above general schemes, each A is independently monocyclic or bicyclic aryl or heteroaryl, optionally substituted with one or more A', each A' is independently lower alkyl, halo, cyano, or heteroaryl, each X is $CH_2$ or O.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano- 1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

General Conditions.

Unless otherwise stated, all temperatures including melting points (i.e., MP) are in degrees Celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

PREPARATIVE EXAMPLES

Example 1

2-((3R,4R)-3-Amino-tetrahydro-pyran-4-ylamino)-thieno[3,2-d]pyrimidine-7-carboxylic acid (6-ethyl-pyridin-2-yl)-amide

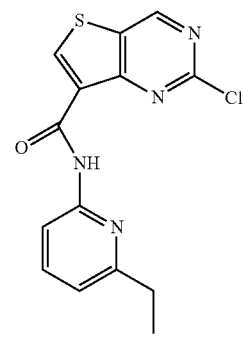 [SMILES: CCc1cccc(NC(=O)c2csc3cnc(Cl)nc23)n1]

Step 1

2-Chloro-thieno[3,2-d]pyrimidine-7-carbonyl chloride

A solution of 2-chloro-thieno[3,2-d]pyrimidine-7-carboxylic acid (0.050 g, 0.235 mmol) in thionyl chloride (2 mL) was refluxed for 3 h. The solvent was concentrated in vacuo and then dried in vacuo to give crude 2-chloro-thieno[3,2-d]pyrimidine-7-carbonyl chloride (0.054 g, 0.23 μmol, 99.5%) as a light yellow solid which was used directly in the next step without further purification.

Step 2

2-Chloro-thieno[3,2-d]pyrimidine-7-carboxylic acid (6-ethyl-pyridin-2-yl)-amide

To a stirred solution of 2-chloro-thieno[3,2-d]pyrimidine-7-carbonyl chloride (0.054 g, 0.233 mmol) and 2-amino-6-ethylpyridine (0.029 g, 0.233 mmol) methylene chloride (2 mL) was added pyridine (0.057 mL, 0.7 mmol). The reaction mixture was stirred under nitrogen at room temperature for 1 h, and then was diluted with EtOAc, washed with aqueous sodium carbonate and brine, then dried (Na$_2$SO$_4$), filtered and concentrated in vacuo in vacuo to give crude 2-chloro-thieno[3,2-d]pyrimidine-7-carboxylic acid (6-ethyl-pyridin-2-yl)-amide (0.060 g, 0.189 mmol, 80.8%) as a light yellow solid which was used directly in the next step without further purification. LCMS m/z [M+H]=319.

Step 3

{(3R,4R)-4-[7-(6-Ethyl-pyridin-2-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid (6-ethyl-pyridin-2-yl)-amide (0.060 g, 0.19 mmol) and tert-butyl (3R,4R)-4-aminotetrahydro-2H-pyran-3-ylcarbamate (0.081 g, 0.38 mmol) in dioxane (3 mL) was added DIPEA (0.099 mL, 0.57 mmol). The reaction mixture was heated at 110° C. overnight. The reaction mixture was cooled then diluted with EtOAc, washed with aqueous sodium carbonate, then brine, dried over anhydrous sodium sulfate, filtered and concentrated in vacuo. The residue obtained was then purified by chromatography (silica, 40 g, 10 to 60% EtOAc in hexanes) to give {(3R,4R)-4-[7-(6-ethyl-pyridin-2-ylcarbamoyl)-thieno[3,2-d]pyrimidin-2-ylamino]-tetrahydro-pyran-3-yl}-carbamic acid tert-butyl ester (0.040 g, 0.080 mmol, 42.6%) as a white solid. LCMS m/z [M+H]=499.

Step 4

2-((3R,4R)-3-Amino-tetrahydro-pyran-4-ylamino)-thieno[3,2-d]pyrimidine-7-carboxylic acid (6-ethyl-pyridin-2-yl)-amide A solution of {(3R,4R)-4-[7-(6-ethyl-pyridin-2-ylcarbamoyl)-thieno[3,2-d]pyrimidin-2-ylamino]-tetrahydro-pyran-3-yl}-carbamic acid tert-butyl ester (0.038 g, 0.076 mmol) in 20% TFA in dichloromethane (3 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 0 to 20% MeOH in dichloromethane) to give 2-((3R,4R)-3-amino-tetrahydro-pyran-4-ylamino)-thieno[3,2-d]pyrimidine-7-carboxylic acid (6-ethyl-pyridin-2-yl)-amide (0.028 g, 0.070 mmol, 92.2%) as a white solid. LCMS m/z [M+H]=399. $^1$H NMR (300 MHz, DMSO-$d_6$) δ: 11.79 (s, 1H), 9.17 (s, 1H), 9.06 (s, 1H), 8.16 (d, J=8.3 Hz, 1H), 7.80 (t, J=7.8 Hz, 1H), 7.39 (br. s., 1H), 7.09 (d, J=7.3 Hz, 1H), 4.37 (br. s., 1H), 3.74-3.93 (m, 1H), 3.69 (d, J=3.3 Hz, 2H), 3.48-3.64 (m, 1H), 3.06 (d, J=3.0 Hz, 1H), 2.77 (q, J=7.6 Hz, 2H), 1.70-2.10 (m, 4H), 1.28 (t, J=7.7 Hz, 3H).

Example 2

2-((1R,2S)-2-Amino-cyclohexylamino)-thieno[3,2-d]pyrimidine-7-carboxylic acid (8-methyl-quinolin-6-yl)-amide

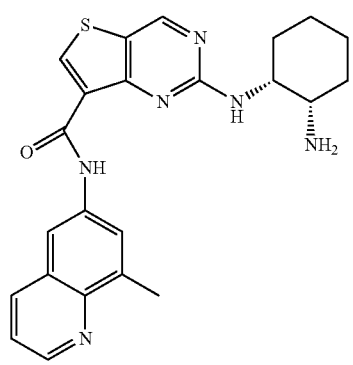 [SMILES: Cc1cc(NC(=O)c2csc3cnc(N[C@@H]4CCCC[C@@H]4N)nc23)cc2cccnc12]

Step 1

2-Chloro-thieno[3,2-d]pyrimidine-7-carbonyl chloride

A solution of 2-chloro-thieno[3,2-d]pyrimidine-7-carboxylic acid (0.150 g, 0.70 mmol) and thionyl chloride (6 mL) was refluxed for 3 h. The solvent was concentrated in vacuo and then dried in vacuo to give 0.16 g of crude 2-chloro-thieno[3,2-d]pyrimidine-7-carbonyl chloride (0.163 g, 0.70 mmol, 100%) as a light yellow solid which was used directly in the next step without further purification.

Step 2

2-Chloro-N-(8-methylquinolin-6-yl)thieno[3,2-d]pyrimidine-7-carboxamide

To a solution of 2-chloro-thieno[3,2-d]pyrimidine-7-carbonyl chloride (0.10 g, 0.43 mmol) and 8-methylquinolin-6-amine (0.068 g, 0.43 mmol) in methylene chloride (4 mL) was added pyridine (0.10 mL, 1.29 mmol). The reaction mixture was stirred under nitrogen at room temperature for 1 h. The reaction mixture was diluted with EtOAc, washed with aqueous sodium carbonate, then brine, dried over anhydrous sodium sulfate, filtered and concentrated to give 0.15 g of crude 2-chloro-N-(8-methylquinolin-6-yl)thieno[3,2-d]pyrimidine-7-carboxamide (0.15 g, 0.42 mmol, 98.5%) as a light yellow solid which was used directly in the next step without further purification. LCMS m/z [M+H]=355.

Step 3

{(1S,2R)-2-[7-(8-Methyl-quinolin-6-ylcarbamoyl)-thieno[3,2-d]pyrimidin-2-ylamino]-cyclohexyl}-carbamic acid tert-butyl ester To a solution of 2-chloro-N-(8-methylquinolin-6-yl)thieno[3,2-d]pyrimidine-7-carboxamide (0.15 g, 0.42 mmol) and N-Boc-1(S),2(R)-diaminocyclohexane (0.14 g, 0.63 mmol) in dioxane (4 mL) was added DIPEA (0.22 mL, 1.27 mmol). The reaction mixture was heated at 115° C. overnight. The reaction mixture was cooled and then diluted with EtOAc, washed with aqueous sodium carbonate, then brine, dried over anhydrous sodium sulfate, filtered and concentrated in vacuo. The residue obtained was then purified by chromatography (silica, 40 g, 80% EtOAc in hexane) to give {(1S,2R)-2-[7-(8-methyl-quinolin-6-ylcarbamoyl)-thieno[3,2-d]pyrimidin-2-ylamino]-cyclohexyl}-carbamic acid tert-butyl ester (0.15 g, 0.28 mmol, 66.6%) as a light yellow solid. LCMS m/z [M+H]=533.

Step 4

2-((1R,2S)-2-amino-cyclohexylamino)-thieno[3,2-d]pyrimidine-7-carboxylic acid (8-methyl-quinolin-6-yl)-amide A solution of {(1S,2R)-2-[7-(8-methyl-quinolin-6-ylcarbamoyl)-thieno[3,2-d]pyrimidin-2-ylamino]-cyclohexyl}-carbamic acid tert-butyl ester (0.150 g, 0.28 mmol) in 20% TFA in dichloromethane (6 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 10 to 30% MeOH in dichloromethane) to give 2-((1R,2S)-2-amino-cyclohexylamino)-thieno[3,2-d]pyrimidine-7-carboxylic acid (8-methyl-quinolin-6-yl)-amide (0.094 g, 0.22 mmol, 77.2%) as a white solid. LCMS m/z [M+H]=433. $^1$H NMR (300 MHz, DMSO-d$_6$) δ: 11.63 (br. s., 1H), 9.16 (s, 1H), 9.03 (s, 1H), 8.85 (dd, J=4.1, 1.6 Hz, 1H), 8.44 (br. s., 1H), 8.30 (dd, J=8.4, 1.4 Hz, 1H), 7.76 (br. s., 1H), 7.54 (dd, J=8.3, 4.0 Hz, 1H), 7.36 (d, J=7.5 Hz, 1H), 4.14 (br. s., 1H), 3.23 (br. s., 1H), 2.76 (s, 3H), 2.14 (br. s., 1H), 1.51-1.90 (m, 5H), 1.38 (br. s., 2H)

Example 3

2-((1R,2S)-2-Amino-cyclohexylamino)-thieno[3,2-d]pyrimidine-7-carboxylic acid (8-ethyl-quinolin-6-yl)-amide

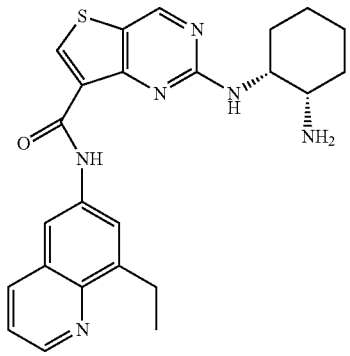 [SMILES: CCc1cc(NC(=O)c2csc3cnc(N[C@@H]4CCCC[C@@H]4N)nc23)cc2cccnc12]

Step 1

N-(2-Ethyl-4-nitrophenyl)acetamide and N-(2-ethyl-5-nitrophenyl)acetamide

Sulfuric acid (30 mL, 563 mmol) was cooled to 0° C. and N-(2-ethylphenyl)acetamide (2 g, 12.3 mmol) was added in several portions. To the resulting solution was added potassium nitrate (1.24 g, 12.3 mmol). The reaction mixture was allowed to warm to room temperature and stirred overnight. The reaction mixture was poured over ice slowly. The resulting solid was collected by filtration to give white solid containing both N-(2-ethyl-4-nitrophenyl)acetamide and N-(2-ethyl-5-nitrophenyl)acetamide (2.0 g, 9.61 mmol, 78.4%) which was directly used for the next step without further purification.

Step 2

2-Ethyl-5-nitroaniline and 2-ethyl-4-nitroaniline

A solution of the mixture of N-(2-ethyl-4-nitrophenyl) acetamide and N-(2-ethyl-5-nitrophenyl)acetamide (2 g, 9.61 mmol) in concentrated hydrobromic acid (40 mL) was heated at 110° C. for 8 h. The reaction mixture was cooled to room temperature. After partial removal of solvent, the mixture was diluted with EtOAc and ice water. Saturated aqueous sodium carbonate was slowly added. The organic phase was washed with sodium carbonate and brine, dried over Na$_2$SO$_4$, filtered and concentrated in vacuo to give the crude mixture of 2-ethyl-5-nitroaniline and 2-ethyl-4-nitroaniline (1.5 g, 9.03 mmol, 94.0%) as a yellow solid which was directly used for the next step without purification.

Step 3

8-Ethyl-6-nitro-quinoline

To a solution of sulfuric acid (4 mL, 75.0 mmol) and water (4 mL) was added sodium 3-nitrobenzenesulfonate (1.35 g, 6.02 mmol) and glycerol (1.77 mL, 24.1 mmol). The resulting solution was stirred at 100° C. and the mixture of 2-ethyl-5-nitroaniline and 2-ethyl-4-nitroaniline (1.00 g, 6.02 mmol) was added. The reaction mixture was stirred at 150° C. for 3 h. After cooling to room temperature, ice was slowly added to the reaction mixture. The mixture was carefully neutralized with saturated sodium carbonate and extracted with EtOAc. The organic phase was washed with saturated sodium carbonate and brine, dried over Na$_2$SO$_4$, filtered and concentrated in vacuo to give the crude product containing both 8-ethyl-5-nitro-quinoline and 8-ethyl-6-nitro-quinoline. The crude product was purified by chromatography (silica, 40 g, 5 to 50% EtOAc in hexanes) to give 8-ethyl-6-nitro-quinoline (0.17 g, 0.84 mmol, 14%) as a yellow solid. LCMS m/z [M+H]=203.

Step 4

8-Ethylquinolin-6-amine

A mixture of 8-ethyl-6-nitroquinoline (0.16 g, 0.79 mmol) and 10% palladium on carbon (0.16 g) in EtOH (5 mL) was shaken in a Parr apparatus under hydrogen (50 psi) for 4 h. The mixture was filtered through celite and then the filtrate concentrated in vacuo. The crude residue was purified by chromatography (silica, 40 g, 5 to 50% EtOAc in hexane) to give 8-ethylquinolin-6-amine (0.023 g, 0.13 mmol, 16.9%) as a gray solid. LCMS m/z [M+H]=173.

Step 5

2-Chloro-thieno[3,2-d]pyrimidine-7-carbonyl chloride

A solution of 2-chloro-thieno[3,2-d]pyrimidine-7-carboxylic acid (0.150 g, 0.70 mmol) and thionyl chloride (6 mL) was refluxed for 3 h. The solvent was concentrated in vacuo and the residue obtained was dried in vacuo to give 2-chloro-thieno[3,2-d]pyrimidine-7-carbonyl chloride (0.163 g, 0.70 mmol, 100%) as a light yellow solid which was used directly in the next step without further purification.

Step 6

2-Chloro-N-(8-ethylquinolin-6-yl)thieno[3,2-d]pyrimidine-7-carboxamide

To a solution of 2-chloro-thieno[3,2-d]pyrimidine-7-carbonyl chloride (0.030 g, 0.129 mmol) and 8-ethylquinolin- 6-amine (0.022 g, 0.129 mmol) in methylene chloride (2 mL) was added pyridine (0.031 mL, 0.31 mmol). The reaction mixture was stirred under nitrogen at room temperature for 1 h. The reaction mixture was diluted with EtOAc, washed with aqueous sodium carbonate and then brine, dried over anhydrous Na$_2$SO$_4$, and finally concentrated to give crude 2-chloro-N-(8-ethylquinolin-6-yl)thieno[3,2-d]pyrimidine-7-carboxamide (0.047 g, 0.128 mmol, 99%) as a light yellow solid which was used directly in the next step without further purification.
LCMS m/z [M+H]=369.

Step 7

{(1S,2R)-2-[7-(8-Ethyl-quinolin-6-ylcarbamoyl)-thieno[3,2-d]pyrimidin-2-ylamino]-cyclohexyl}-carbamic acid tert-butyl ester To a solution of 2-chloro-N-(8-ethylquinolin-6-yl)thieno[3,2-d]pyrimidine-7-carboxamide (0.047 g, 0.128 mmol) and N-Boc-1(S),2(R)-diaminocyclohexane (0.041 g, 0.19 mmol) in dioxane (4 mL) was added DIPEA (0.067 mL, 0.38 mmol). The reaction mixture was heated at 115° C. overnight. The reaction mixture was cooled and then diluted with EtOAc, washed with aqueous sodium carbonate, then brine, dried over anhydrous sodium sulfate, filtered and concentrated in vacuo. The residue obtained was then purified by chromatography (silica, 40 g, EtOAc) to give {(1S,2R)-2-[7-(8-Ethyl-quinolin-6-ylcarbamoyl)-thieno[3,2-d]pyrimidin-2-ylamino]-cyclohexyl}-carbamic acid tert-butyl ester (0.040 g, 0.073 mmol, 57.4%) as a light yellow solid. LCMS m/z [M+H]=547.

Step 8

2-((1R,2S)-2-Amino-cyclohexylamino)-thieno[3,2-d]pyrimidine-7-carboxylic acid (8-ethyl-quinolin-6-yl)-amide A solution of {(1S,2R)-2-[7-(8-Ethyl-quinolin-6-ylcarbamoyl)-thieno[3,2-d]pyrimidin-2-ylamino]-cyclohexyl}-carbamic acid tert-butyl ester (0.038 g, 0.070 mmol) in 20% TFA in dichloromethane (6 mL) was stirred at room temperature for 30 min. The mixture was concentrated in vacuo then EtOAc and aqueous sodium carbonate were added. The organic layer was were washed with aqueous sodium carbonate then brine, dried over anhydrous sodium sulfate, filtered and concentrated in vacuo and finally purified by chromatography (silica, 40 g, 10 to 30% MeOH in dichloromethane) to give 2-((1R,2S)-2-amino-cyclohexylamino)-thieno[3,2-d]pyrimidine-7-carboxylic acid (8-ethyl-quinolin-6-yl)-amide (0.019 g, 0.43 mmol, 61.2%) as a white solid. LCMS m/z [M+H]=447. $^1$H NMR (300 MHz, DMSO-d$_6$) δ: 11.62 (s, 1H), 9.16 (s, 1H), 9.03 (s, 1H), 8.85 (dd, J=4.0, 1.8 Hz, 1H), 8.44 (d, J=2.0 Hz, 1H), 8.30 (dd, J=8.4, 1.4 Hz, 1H), 7.76 (br. s., 1H), 7.53 (dd, J=8.3, 4.3 Hz, 1H), 7.35 (d, J=7.5 Hz, 1H), 4.13 (br. s., 1H), 3.35-3.42 (m, 1H), 3.18-3.28 (m, 2H), 1.49-2.01 (m, 8H), 1.34 (t, J=7.5 Hz, 3H).

Example 4

2-((1R,2S)-2-Amino-cyclohexylamino)-thieno[3,2-d]pyrimidine-7-carboxylic acid (5-cyano-6-methyl-pyridin-2-yl)-amide

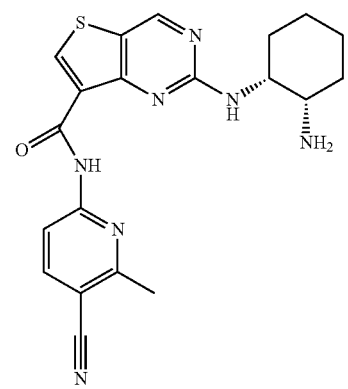 [SMILES: Cc1nc(NC(=O)c2csc3cnc(N[C@@H]4CCCC[C@@H]4N)nc23)ccc1C#N]

Step 1

2-Chloro-thieno[3,2-d]pyrimidine-7-carbonyl chloride

A solution of 2-chloro-thieno[3,2-d]pyrimidine-7-carboxylic acid (0.050 g, 0.235 mmol) in thionyl chloride (2 mL) was refluxed for 3 h. The mixture was cooled then concentrated and dried in vacuo to give crude 2-chloro-thieno[3,2-d]pyrimidine-7-carbonyl chloride (0.054 g, 0.231 mmol, 99.5%) as a light yellow solid which was used directly in the next step without further purification.

Step 2

2-Chloro-N-(5-cyano-6-methylpyridin-2-yl)thieno[3,2-d]pyrimidine-7-carboxamide

To a solution of 2-chloro-thieno[3,2-d]pyrimidine-7-carbonyl chloride (0.10 g, 0.429 mmol) and 6-amino-2-methylnicotinonitrile (0.057 g, 0.429 mmol) in methylene chloride (4 mL) was added pyridine (0.10 mL, 01.29 mmol). The reaction mixture was stirred at room temperature for 1 h. The reaction mixture was diluted with EtOAc, washed with aqueous sodium carbonate, then brine, dried over anhydrous Na$_2$SO$_4$, and finally concentrated to give crude 2-chloro-N-(5-cyano-6-methylpyridin-2-yl)thieno[3,2-d]pyrimidine-7-carboxamide (0.12 g, 0.36 mmol, 84.8%) as a light yellow solid which was used directly in the next step without further purification. LCMS m/z [M+H]=330.

Step 3

{(3R,4R)-4-[7-(6-Ethyl-pyridin-2-ylcarbamoyl)-thieno[3,2-d]pyrimidin-2-ylamino]-tetrahydro-pyran-3-yl}-carbamic acid tert-butyl ester To a suspension of 2-chloro-N-(5-cyano-6-methylpyridin-2-yl)thieno[3,2-d]pyrimidine-7-carboxamide (0.120 g, 0.36 mmol) and N-Boc-1(S),2(R)-diaminocyclohexane (0.12 g, 0.55 mmol) in dioxane (4 mL) was added DIPEA (0.19 mL, 1.09 mmol). The reaction mixture was heated at 115° C.

overnight. The reaction mixture was cooled and then diluted with EtOAc, washed with aqueous sodium carbonate, then brine, dried over anhydrous sodium sulfate, filtered and concentrated in vacuo. The residue obtained was then purified by chromatography (silica, 40 g, EtOAc) to give {(3R, 4R)-4-[7-(6-ethyl-pyridin-2-ylcarbamoyl)-thieno[3,2-d]pyrimidin-2-ylamino]-tetrahydro-pyran-3-yl}-carbamic acid tert-butyl ester (0.12 g, 0.24 mmol, 65%) as a white solid. LCMS m/z [M+H]=508.

Step 4

2-((1R,2S)-2-Amino-cyclohexylamino)-thieno[3,2-d]pyrimidine-7-carboxylic acid (5-cyano-6-methyl-pyridin-2-yl)-amide A solution of tert-butyl (1S,2R)-2-(7-(5-cyano-6-methyl-pyridin-2-ylcarbamoyl)thieno[3,2-d]pyrimidin-2-ylamino)cyclohexylcarbamate (0.12 g, 0.24 mmol) in 20% TFA in dichloromethane (6 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 5 to 30% MeOH in dichloromethane) to give 2-((1R,2S)-2-amino-cyclohexylamino)-thieno[3,2-d]pyrimidine-7-carboxylic acid (5-cyano-6-methyl-pyridin-2-yl)-amide (0.077 g, 0.19 mmol, 79.9%) as a white solid. LCMS m/z [M+H]=408. $^1$H NMR (300 MHz, DMSO-d$_6$) δ: 9.14 (s, 1H), 9.10 (s, 1H), 8.22-8.34 (m, 2H), 7.27-7.43 (m, 1H), 4.12-4.25 (m, 1H), 3.07-3.20 (m, 1H), 2.65 (s, 3H), 1.28-1.85 (m, 8H).

Example 5

2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide

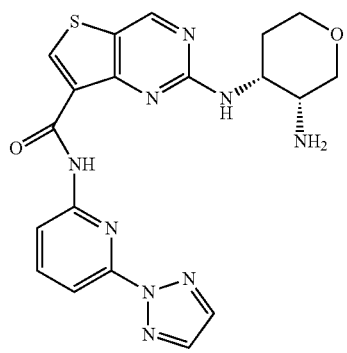 [SMILES: N[C@H]1COCC[C@H]1Nc1ncc2scc(C(=O)Nc3cccc(-n4nccn4)n3)c2n1]

Step 1

6-(2H-1,2,3-triazol-2-yl)pyridin-2-amine and 6-(2H-1,2,3-triazol-1-yl)pyridin-2-amine A mixture of 6-(di-Boc-amino)-2-bromopyridine (0.40 g, 1.07 mmol), 2H-1,2,3-triazole (0.74 g, 10.7 mmol), potassium hydroxide (0.12 g, 2.14 mmol) and copper (0.41 g, 2.14 mmol) were stirred in a pressure tube at 150° C. overnight. After cooling, EtOAc was added with stirring. After removal of the solid by filtration, the organic layer was washed with aqueous sodium carbonate and brine, dried over Na$_2$SO$_4$, and then concentrated in vacuo. The crude material was purified by chromatography (silica, 40 g, 40 to 60% EtOAc in hexanes) to give 6-(2H-1,2,3-triazol-2-yl)pyridin-2-amine (0.080 g, 0.50 mmol, 46.3%) as a white solid and 6-(2H-1,2,3-triazol-1-yl)pyridin-2-amine (0.071 g, 0.44 mmol, 41.1%) as a white solid.

Step 2

2-Chloro-thieno[3,2-d]pyrimidine-7-carbonyl chloride

A solution of 2-chloro-thieno[3,2-d]pyrimidine-7-carboxylic acid (0.050 g, 0.235 mmol) in thionyl chloride (2 mL) was refluxed for 3 h. The solvent was removed in vacuo and then the residue dried in vacuo to give crude 2-chloro-thieno[3,2-d]pyrimidine-7-carbonyl chloride (0.054 g, 0.231 mmol, 99.5%) as a light yellow solid which was used directly in the next step without further purification.

Step 3

N-(6-(2H-1,2,3-triazol-2-yl)pyridin-2-yl)-2-chlorothieno[3,2-d]pyrimidine-7-carboxamide To a solution of 2-chloro-thieno[3,2-d]pyrimidine-7-carbonyl chloride (0.10 g, 0.43 mmol) and 6-(2H-1,2,3-triazol-2-yl)pyridin-2-amine (0.69 g, 0.43 mmol) in methylene chloride (4 mL) was added pyridine (0.10 mL, 1.29 mmol). The reaction mixture was stirred at room temperature for 1 h. The reaction mixture was diluted with EtOAc, washed with aqueous sodium carbonate, then brine, dried over anhydrous sodium sulfate, filtered and concentrated and purified by (silica, 40 g, 80% EtOAc in hexane) to give N-(6-(2H-1,2,3-triazol-2-yl)pyridin-2-yl)-2-chlorothieno[3,2-d]pyrimidine-7-carboxamide (0.09 g, 0.25 mmol, 58.6%) as a white solid.
LCMS m/z [M+H]=358.

Step 4 tert-Butyl (3R,4R)-4-(7-(6-(2H-1,2,3-triazol-2-yl)pyridin-2-ylcarbamoyl)thieno[3,2-d]pyrimidin-2-ylamino)tetrahydro-2H-pyran-3-ylcarbamate To a suspension of N-(6-(2H-1,2,3-triazol-2-yl)pyridin-2-yl)-2-chlorothieno[3,2-d]pyrimidine-7-carboxamide (0.09 g, 0.25 mmol) and tert-butyl (3R,4R)-4-aminotetrahydro-2H-pyran-3-ylcarbamate (0.11 g, 0.50 mmol) in dioxane (3 mL) was added DIPEA (0.13 mL, 0.76 mmol). The reaction mixture was heated at 115° C. overnight. The reaction mixture was cooled and then diluted with EtOAc, washed with aqueous sodium carbonate, then brine, dried over anhydrous sodium sulfate, filtered and concentrated in vacuo. The residue obtained was then purified by chromatography (silica, 40 g, EtOAc) to give tert-butyl (3R,4R)-4-(7-(6-(2H-1,2,3-triazol-2-yl)pyridin-2-ylcarbamoyl)thieno[3,2-d]pyrimidin-2-ylamino)tetrahydro-2H-pyran-3-ylcarbamate (0.085 g, 0.16 mmol, 62.9%) as a white solid. LCMS m/z [M+H]=538.

Step 5

2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide A solution of tert-butyl (3R,4R)-4-(7-(6-(2H-1,2,3-triazol-2-yl)pyridin-2-ylcarbamoyl)thieno[3,2-d]pyrimidin-2- ylamino)tetrahydro-2H-pyran-3-ylcarbamate (0.085 g, 0.16 mmol) in 20% TFA in dichloromethane (6 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 5 to 30% MeOH in dichloromethane) to give 2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide (0.065 g, 0.15 mmol, 94.0%) as a white solid. LCMS m/z [M+H]=438. $^1$H NMR (300 MHz, DMSO-$d_6$) δ: 11.74-12.30 (m, 1H), 9.18 (s, 1H), 9.11 (s, 1H), 8.39 (d, J=8.3 Hz, 1H), 8.20 (s, 2H), 8.14 (s, 1H), 7.79 (d, J=8.0 Hz, 1H), 7.30-7.55 (m, 1H), 4.37 (br. s., 1H), 3.41-3.73 (m, 4H), 3.12 (br. s., 1H), 1.60-2.08 (m, 4H)

Example 6

2-((3R,4R)-3-Amino-tetrahydro-pyran-4-ylamino)-thieno[3,2-d]pyrimidine-7-carboxylic acid (6-[1,2,3]triazol-1-yl-pyridin-2-yl)-amide

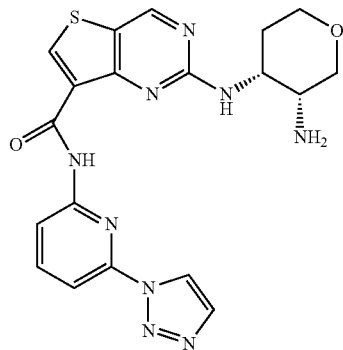 [SMILES: N[C@H]1COCC[C@H]1Nc1ncc2scc(C(=O)Nc3cccc(-n4ccnn4)n3)c2n1]

Step 1

2-Chloro-thieno[3,2-d]pyrimidine-7-carbonyl chloride

A solution of 2-chloro-thieno[3,2-d]pyrimidine-7-carboxylic acid (0.050 g, 0.235 mmol) in thionyl chloride (2 mL) was refluxed for 3 h. The mixture was cooled, concentrated and then dried in vacuo to give crude 2-chloro-thieno[3,2-d]pyrimidine-7-carbonyl chloride (0.054 g, 0.231 mmol, 99.5%) as a light yellow solid which was used directly in the next step without further purification.

Step 2

N-(6-(2H-1,2,3-Triazol-1-yl)pyridin-2-yl)-2-chlorothieno[3,2-d]pyrimidine-7-carboxamide To a solution of 2-chloro-thieno[3,2-d]pyrimidine-7-carbonyl chloride (0.10 g, 0.43 mmol) and 6-(2H-1,2,3-triazol-1-yl)pyridin-2-amine (0.69 g, 0.43 mmol) in methylene chloride (4 mL) was added pyridine (0.10 mL, 1.29 mmol). The reaction mixture was stirred under nitrogen at room temperature for 1 h. The reaction mixture was diluted with EtOAc, washed with aqueous sodium carbonate, then brine, dried over anhydrous Na$_2$SO$_4$, and finally concentrated to give crude of N-(6-(2H-1,2,3-triazol-1-yl)pyridin-2-yl)-2-chlorothieno[3,2-d]pyrimidine-7-carboxamide (0.13 g, 0.38 mmol, 87.3%) as a white solid which was directly used for the next step without purification. LCMS m/z [M+H]=358.

Step 3 tert-Butyl (3R,4R)-4-(7-(6-(2H-1,2,3-triazol-1-yl)pyridin-2-ylcarbamoyl)thieno[3,2-d]pyrimidin-2-ylamino)tetrahydro-2H-pyran-3-ylcarbamate To a suspension of N-(6-(2H-1,2,3-triazol-1-yl)pyridin-2-yl)-2-chlorothieno[3,2-d]pyrimidine-7-carboxamide (0.13 g, 0.38 mmol) and tert-butyl (3R,4R)-4-aminotetrahydro-2H-pyran-3-ylcarbamate (0.12 g, 0.56 mmol) in dioxane (3 mL) was added DIPEA (0.20 mL, 1.12 mmol). The reaction mixture was heated at 115° C. overnight. The reaction mixture was cooled then diluted with EtOAc, washed with aqueous sodium carbonate, then brine, and then dried over anhydrous Na$_2$SO$_4$. The organic phase was concentrated and purified by chromatography (silica, 40 g, EtOAc) to give tert-butyl (3R,4R)-4-(7-(6-(2H-1,2,3-triazol-1-yl)pyridin-2-ylcarbamoyl)thieno[3,2-d]pyrimidin-2-ylamino)tetrahydro-2H-pyran-3-ylcarbamate (0.065 g, 0.12 mmol, 32.3%) as a white solid. LCMS m/z [M+H]=538.

Step 4

2-((3R,4R)-3-Amino-tetrahydro-pyran-4-ylamino)-thieno[3,2-d]pyrimidine-7-carboxylic acid (6-[1,2,3]triazol-1-yl-pyridin-2-yl)-amide A solution of tert-butyl (3R,4R)-4-(7-(6-(2H-1,2,3-triazol-1-yl)pyridin-2-ylcarbamoyl)thieno[3,2-d]pyrimidin-2-ylamino)tetrahydro-2H-pyran-3-ylcarbamate (0.060 g, 0.11 mmol) in 20% TFA in dichloromethane (6 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 5 to 30% MeOH in dichloromethane) to give 2-((3R,4R)-3-amino-tetrahydro-pyran-4-ylamino)-thieno[3,2-d]pyrimidine-7-carboxylic acid (6-[1,2,3]triazol-1-yl-pyridin-2-yl)-amide (0.018 g, 0.041 mmol, 36.9%) as a white solid. LCMS m/z [M+H]=438.

$^1$H NMR (300 MHz, DMSO-$d_6$) δ: 11.77-12.31 (m, 1H), 9.19 (s, 1H), 9.13 (s, 1H), 8.88 (br. s., 1H), 8.38 (d, J=8.3 Hz, 1H), 8.20 (t, J=8.0 Hz, 1H), 8.06 (s, 1H), 7.84 (d, J=7.5 Hz, 1H), 7.24-7.56 (m, 1H), 4.26 (br. s., 1H), 3.50 (br. s., 2H), 3.11-3.24 (m, 1H), 3.03 (br. s., 1H), 1.55-2.00 (m, 4H)

Example 7

2-((1R,2S)-2-Amino-cyclohexylamino)-thieno[3,2-d]pyrimidine-7-carboxylic acid [1,6]naphthyridin-2-ylamide

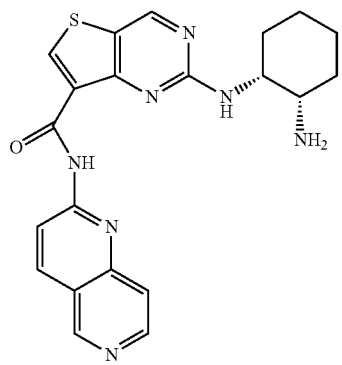 [SMILES: N[C@H]1CCCC[C@H]1Nc1ncc2scc(C(=O)Nc3ccc4cnccc4n3)c2n1]

Step 1

2-Chloro-N-(1,6-naphthyridin-2-yl)thieno[3,2-d]pyrimidine-7-carboxamide

To a solution of 2-chloro-thieno[3,2-d]pyrimidine-7-carboxylic acid (0.10 g, 0.47 mmol) and 1,6-naphthyridin-2-amine (0.068 g, 0.47 mmol) in pyridine (5 mL) was slowly added $POCl_3$ (0.13 mL, 1.4 mmol). The reaction mixture was stirred under nitrogen at room temperature for 1 h. The reaction mixture was diluted with EtOAc, washed with aqueous sodium carbonate, then brine, dried over anhydrous sodium sulfate, filtered and concentrated in vacuo. The residue obtained was then purified by chromatography (silica, 40 g, EtOAc) to give 2-chloro-N-(1,6-naphthyridin-2-yl)thieno[3,2-d]pyrimidine-7-carboxamide (0.080 g, 0.24 mmol, 50.2%) as a white solid. LCMS m/z [M+H]=342.

Step 2 tert-Butyl (1S,2R)-2-(7-(1,6-naphthyridin-2-ylcarbamoyl)thieno[3,2-d]pyrimidin-2-ylamino)cyclohexylcarbamate To a suspension of 2-chloro-N-(1,6-naphthyridin-2-yl)thieno[3,2-d]pyrimidine-7-carboxamide (0.080 g, 0.24 mmol) and N-Boc-1(S),2(R)-diaminocyclohexane (0.10 g, 0.47 mmol) in dioxane (4 mL) was added DIPEA (0.12 mL, 0.70 mmol). The reaction mixture was heated at 115° C. overnight. The reaction mixture was cooled and then diluted with EtOAc, washed with aqueous sodium carbonate, then brine, dried over anhydrous sodium sulfate, filtered and concentrated in vacuo. The residue obtained was then purified by chromatography (silica, 40 g, EtOAc) to give tert-butyl (1S,2R)-2-(7-(1,6-naphthyridin-2-ylcarbamoyl)thieno[3,2-d]pyrimidin-2-ylamino)cyclohexylcarbamate (0.067 g, 0.013 mmol, 55.1%) as a light yellow solid. LCMS m/z [M+H]=520.

Step 3

2-((1R,2S)-2-Amino-cyclohexylamino)-thieno[3,2-d]pyrimidine-7-carboxylic acid [1,6]naphthyridin-2-ylamide A solution of tert-butyl (1S,2R)-2-(7-(1,6-naphthyridin-2-ylcarbamoyl)thieno[3,2-d]pyrimidin-2-ylamino)cyclohexylcarbamate (0.067 g, 0.13 mmol) in 20% TFA in dichloromethane (5 mL) was stirred at room temperature for 30 min. The mixture was concentrated in vacuo then EtOAc and aqueous sodium carbonate were added. The organic layer was washed with aqueous sodium carbonate, then brine, dried over anhydrous sodium sulfate, filtered and concentrated in vacuo. The residue obtained was then purified by chromatography (silica, 40 g, 10 to 30% MeOH in dichloromethane) to give 2-((1R,2S)-2-amino-cyclohexylamino)-thieno[3,2-d]pyrimidine-7-carboxylic acid [1,6]naphthyridin-2-ylamide (0.017 g, 0.041 mmol, 31.4%) as a white solid. LCMS m/z [M+H]=420. $^1$H NMR (300 MHz, DMSO-$d_6$) δ: 9.31 (s, 1H), 9.17 (s, 1H), 9.15 (s, 1H), 8.60-8.76 (m, 3H), 7.64 (d, J=6.0 Hz, 1H), 7.34-7.46 (m, 1H), 4.35 (br. s., 1H), 3.26 (br. s., 1H), 1.37-1.94 (m, 8H).

Example 8

2-(cis-2-Amino-cyclohexylamino)-thieno[3,2-d]pyrimidine-7-carboxylic acid benzothiazol-2-ylamide

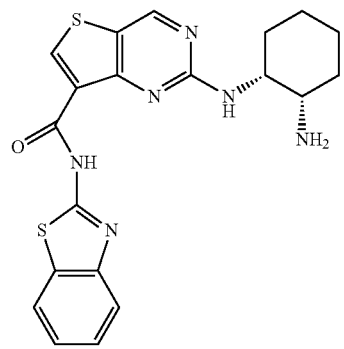 [SMILES: N[C@H]1CCCC[C@H]1Nc1ncc2scc(C(=O)Nc3nc4ccccc4s3)c2n1]

Step 1

N-(Benzo[d]thiazol-2-yl)-2-chlorothieno[3,2-d]pyrimidine-7-carboxamide

To a solution of 2-chloro-thieno[3,2-d]pyrimidine-7-carboxylic acid (0.050 g, 0.23 mmol), 2-aminobenzothiazole (0.035 g, 0.23 mmol) and diisopropylethylamine (0.12 ml, 0.7 mmol) and dimethylformamide (2 mL) was added O-(benzotriazol-1-yl)-N,N,N',N'-bis(tetramethylene)uronium hexafluorophosphate (0.12 g, 0.28 mmol). The mixture was stirred at room temperature for 1 h. The reaction were diluted with EtOAc and was washed with aqueous sodium carbonate, brine, dried over anhydrous sodium sulfate, filtered and concentrated in vacuo under reduced pressure to give crude N-(benzo[d]thiazol-2-yl)-2-chlorothieno[3,2-d]pyrimidine-7-carboxamide (0.081 g, 0.23 mmol, 100%) as a slight yellow solid, which was used for the next step without further purification. LCMS m/z [M+H]=347.

Step 2

2-(cis-2-Amino-cyclohexylamino)-thieno[3,2-d]pyrimidine-7-carboxylic acid benzothiazol-2-ylamide A suspension of the mixture of N-(benzo[d]thiazol-2-yl)-2-chlorothieno[3,2-d]pyrimidine-7-carboxamide (0.081 g, 0.23 mmol) and cis-1,2-diaminocyclohexane (0.084 mL, 0.70 mmol) in THF (3 mL) was stirred at 65° C. for 1 h. The reaction mixture was cooled and then diluted with EtOAc and the organic layer was washed with aqueous sodium carbonate, brine, dried over anhydrous sodium sulfate, filtered and concentrated in vacuo under reduced pressure. The crude material was purified by chromatography (silica, 40 g, 5% to 30% MeOH in $CH_2Cl_2$) to give 2-(cis-2-amino-cyclohexylamino)-thieno[3,2-d]pyrimidine-7-carboxylic acid benzothiazol-2-ylamide (0.014 g, 0.032 mmol, 14.1%) as a light yellow solid. LCMS m/z [M+H]=425. $^1$H NMR (300 MHz, DMSO-$d_6$) δ: 9.25 (s, 1H), 9.23 (s, 1H), 8.06 (d, J=7.8 Hz, 1H), 7.66-7.82 (m, 2H), 7.49 (t, J=7.7 Hz, 1H), 7.30-7.41 (m, 1H), 4.21-4.36 (m, 1H), 3.59-3.72 (m, 1H), 1.75 (m, 8H)

Example 9

2-(cis-2-Amino-cyclohexylamino)-thieno[3,2-d]pyrimidine-7-carboxylic acid (1H-benzoimidazol-2-yl)-amide

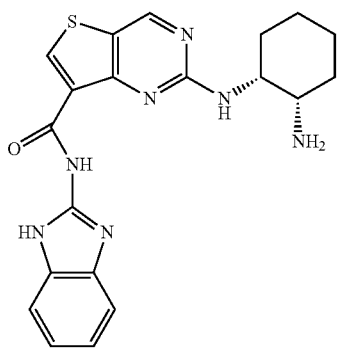 [SMILES: N[C@H]1CCCC[C@H]1Nc1ncc2scc(C(=O)Nc3nc4ccccc4[nH]3)c2n1]

Step 1

N-(Benzo[d]thiazol-2-yl)-2-chlorothieno[3,2-d]pyrimidine-7-carboxamide

To a solution of 2-chloro-thieno[3,2-d]pyrimidine-7-carboxylic acid (0.050 g, 0.23 mmol), 2-aminobenzimidazole (0.031 g, 0.23 mmol) and diisopropylethylamine (0.12 mL, 0.7 mmol) and dimethylformamide (2 mL) was added 2-(7-aza-1H-benzotriazole-1-yl)-1,1,3,3-tetramethyluronium hexafluorophosphate (0.11 g, 0.28 mmol). The mixture was stirred at room temperature for 12 hr. The reaction were diluted with EtOAc and was washed with aqueous sodium carbonate, brine, dried over anhydrous sodium sulfate, filtered and concentrated in vacuo under reduced pressure to give crude N-(benzo[d]thiazol-2-yl)-2-chlorothieno[3,2-d]pyrimidine-7-carboxamide (0.080 g, 0.12 mmol, 50%) as a slight yellow solid, which was used for the next step without further purification. LCMS m/z [M+H]=330.

Step 2

2-(cis-2-Amino-cyclohexylamino)-thieno[3,2-d]pyrimidine-7-carboxylic acid (1H-benzoimidazol-2-yl)-amide A suspension of the mixture of crude N-(1H-benzo[d]imidazol-2-yl)-2-chlorothieno[3,2-d]pyrimidine-7-carboxamide (0.080 g, 0.12 mmol) and cis-1,2-diaminocyclohexane (0.044 mL, 0.36 mmol) in dioxane (3 mL) was stirred at 50° C. for 30 min. The reaction mixture was cooled and then diluted with EtOAc and the organic layer was washed with aqueous sodium carbonate, brine, dried over anhydrous sodium sulfate, filtered and concentrated in vacuo under reduced pressure. The crude material was purified by chromatography (silica, 40 g, 1% to 20% MeOH in $CH_2Cl_2$) to give 2-(cis-2-amino-cyclohexylamino)-thieno[3,2-d]pyrimidine-7-carboxylic acid (1H-benzoimidazol-2-yl)-amide (0.010 g, 0.024 mmol, 20.2%) as a light yellow solid. LCMS m/z [M+H]=408. $^1$H NMR (300 MHz, DMSO-$d_6$) δ: 12.33 (br. s., 1H), 9.28 (s, 1H), 9.22 (s, 1H), 7.69-7.84 (m, 1H), 7.37-7.61 (m, 2H), 7.28-7.35 (m, 1H), 7.14 (d, J=3.5 Hz, 2H), 4.28-4.47 (m, 1H), 3.75-3.93 (m, 1H), 1.43-2.03 (m, 8H).

Example 10

2-((1R,2S)-2-Amino-cyclohexylamino)-thieno[3,2-d]pyrimidine-7-carboxylic acid [1,6]naphthyridin-2-ylamide

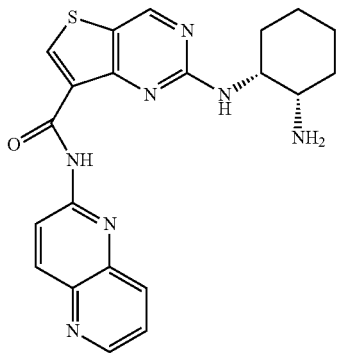 [SMILES: N[C@H]1CCCC[C@H]1Nc1ncc2scc(C(=O)Nc3ccc4ncccc4n3)c2n1]

Step 1

2-Chloro-N-(1,5-naphthyridin-2-yl)thieno[3,2-d]pyrimidine-7-carboxamide

To a solution of 2-chloro-thieno[3,2-d]pyrimidine-7-carboxylic acid (0.050 g, 0.23 mmol), 1,5-naphthyridin-2-amine (0.034 g, 0.23 mmol) and of diisopropylethylamine (0.12 ml, 0.7 mmol) and dimethylformamide (2 mL) was added 2-(7-aza-1H-benzotriazole-1-yl)-1,1,3,3-tetramethyluronium hexafluorophosphate (0.11 g, 0.28 mmol). The mixture was stirred at room temperature for 12 h. The reaction were diluted with EtOAc and was washed with aqueous sodium carbonate, brine, dried over anhydrous sodium sulfate, filtered and concentrated in vacuo under reduced pressure to give crude 2-chloro-N-(1,5-naphthyridin-2-yl)thieno[3,2-d]pyrimidine-7-carboxamide (0.081 g, 0.23 mmol, 100%) as a yellow solid. LCMS m/z [M+H]=342.

Step 2

2-((1R,2S)-2-Amino-cyclohexylamino)-thieno[3,2-d]pyrimidine-7-carboxylic acid [1,5]naphthyridin-2-ylamide To a suspension of 2-chloro-N-(1,5-naphthyridin-2-yl)thieno[3,2-d]pyrimidine-7-carboxamide (0.080 g, 0.23 mmol) in THF (3 mL) was added cis-cyclohexane-1,2-diamine (0.085 mL, 0.071 mmol). The mixture was heated at 60° C. for 3 h. The reaction mixture was cooled and then diluted with EtOAc and the organic layer was washed with aqueous sodium carbonate, brine, dried over anhydrous sodium sulfate, filtered and concentrated in vacuo under reduced pressure. The crude material was purified by chromatography (silica, 40 g, 5% to 30% MeOH in $CH_2Cl_2$) to give 2-((1R,2S)-2-amino-cyclohexylamino)-thieno[3,2-d]pyrimidine-7-carboxylic acid [1,5]naphthyridin-2-ylamide (0.020 g, 0.048 mmol, 20.1%) as a light yellow solid. LCMS m/z [M+H]=420. $^1$H NMR (300 MHz, DMSO-$d_6$) δ: 9.25 (s, 1H), 9.19 (s, 1H), 8.87-8.97 (m, 1H), 8.80 (d, J=9.2 Hz, 1H), 8.54 (d, J=9.2 Hz, 1H), 8.22 (d, J=8.5 Hz, 1H), 7.81 (dd, J=8.5, 4.1 Hz, 1H), 7.64 (br. s., 1H), 4.50-4.68 (m, 1H), 3.62-3.81 (m, 1H), 2.95-3.13 (m, 1H), 1.75 (m, 8H)

Example 11

2-((3R,4R)-3-Amino-tetrahydro-pyran-4-ylamino)-thieno[3,2-d]pyrimidine-7-carboxylic acid (1-methyl-1H-benzoimidazol-4-yl)-amide; hydrochloride

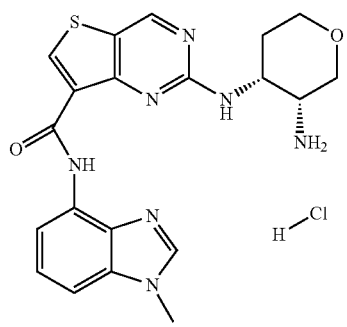 [SMILES: Cn1cnc2c(NC(=O)c3csc4cnc(N[C@@H]5CCOC[C@@H]5N)nc34)cccc21 ; Cl]

Step 1

2-Chloro-thieno[3,2-d]pyrimidine-7-carboxylic acid (1-methyl-1H-benzoimidazol-4-yl)-amide To a solution of 2-chloro-thieno[3,2-d]pyrimidine-7-carboxylic acid (0.050 g, 0.233 mmol) in dimethylformamide (2 mL) was added 1-methyl-1H-benzo[d]imidazole-4-amine (0.068 g, 0.466 mmol), DIPEA (0.122 mL) and 1-((1H-benzo[d][1,2,3]triazol-1-yloxy)(pyrrolidin-1-yl)methylene)pyrrolidinium hexafluorophosphate(V) (0.111 g, 0.256 mmol). The reaction mixture was stirred under nitrogen at room temperature for overnight. The reaction mixture was diluted with water and dichloromethane. The organic layer was separated, washed with aqueous sodium carbonate, then brine, dried over anhydrous sodium sulfate, filtered and concentrated in vacuo. The residue obtained was then purified by chromatography (silica, 40 g, 50 to 90% EtOAc in hexanes) to give 2-chloro-thieno[3,2-d]pyrimidine-7-carboxylic acid (1-methyl-1H-benzoimidazol-4-yl)-amide (0.037 g, 0.107 mmol, 46%) as a yellow solid. LCMS m/z [M+H]=344.

Step 2

2-{(3R,4R)-4-[7-(1-Methyl-1H-benzoimidazol-4-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid (1-methyl-1H-benzoimidazol-4-yl)-amide (0.037 g, 0.108 mmol) and tert-butyl (3R,4R)-4-aminotetrahydro-2H-pyran-3-ylcarbamate (0.035 g, 0.161 mmol) in dioxane (3 mL) was added triethylamine (0.075 mL, 0.538 mmol). The reaction mixture was heated at 100° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 5% 0.7N ammonia in MeOH in dichloromethane) to give {(3R,4R)-4-[7-(1-methyl-1H-benzoimidazol-4-ylcarbamoyl)-thieno[3,2-d]pyrimidin-2-ylamino]-tetrahydro-pyran-3-yl}-carbamic acid tert-butyl ester (0.050 g, 0.095 mmol, 88.8%) as a light orange solid. LCMS m/z [M+H]=524.

Step 3

2-((3R,4R)-3-Amino-tetrahydro-pyran-4-ylamino)-thieno[3,2-d]pyrimidine-7-carboxylic acid (1-methyl-1H-benzoimidazol-4-yl)-amide hydrochloride A solution of {(3R,4R)-4-[7-(1-methyl-1H-benzoimidazol-4-ylcarbamoyl)-thieno[3,2-d]pyrimidin-2-ylamino]-tetrahydro-pyran-3-yl}-carbamic acid tert-butyl ester (0.050 g, 0.096 mmol) in 4M HCl in dioxane (2 mL) was stirred at room temperature overnight. The mixture was concentrated in vacuo then the crude residue was washed with ether twice, concentrated and then dried to give 2-((3R,4R)-3-Amino-tetrahydro-pyran-4-ylamino)-thieno[3,2-d]pyrimidine-7-carboxylic acid (1-methyl-1H-benzoimidazol-4-yl)-amide hydrochloride (0.048 g, 0.104 mmol, 100%) as a brown solid.
$^1$H NMR (DMSO) d: 11.54 (br. s., 2H), 9.26 (s, 1H), 9.11 (s, 1H), 8.63 (br. s., 4H), 8.17 (br. s., 3H), 7.72 (br. s., 1H), 7.45 (br. s., 1H), 4.98 (br. s., 1H), 1.94-2.14 (m, 3H), 1.76-1.92 (m, 3H).
LCMS m/z [M+H]=424.

Example 12

2-(2-Amino-ethylamino)-thieno[3,2-d]pyrimidine-7-carboxylic acid (1-methyl-1H-benzoimidazol-4-yl)-amide; trifluoro-acetic acid

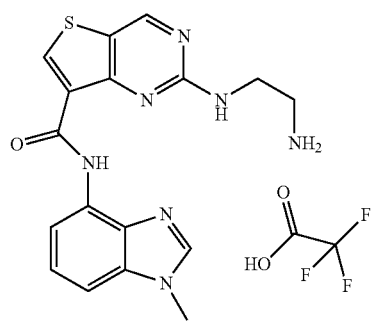

2-(2-Amino-ethylamino)-thieno[3,2-d]pyrimidine-7-carboxylic acid (1-methyl-1H-benzoimidazol-4-yl)-amide trifluoro-acetic acid To a solution of 2-chloro-thieno[3,2-d]pyrimidine-7-carboxylic acid (1-methyl-1H-benzoimidazol-4-yl)-amide (0.035 g, 0.102 mmol) in dioxane (2 mL) was added ethane-1,2-diamine (0.0367 g, 0.611 mmol). The reaction mixture was heated at 80° C. for 3 h. The reaction mixture was concentrated in vacuo. The residue was dissolved with acetonitrile (2 mL), water (1 mL) and concentrated in vacuo HCl (2 drops). The crude product was purified by preparative HPLC (0 to 50% acetonitrile in water with 0.05% TFA) to give 2-(2-amino-ethylamino)-thieno[3,2-d]pyrimidine-7-carboxylic acid (1-methyl-1H-benzoimidazol-4-yl)-amide trifluoro-acetic acid (0.025 g, 0.052 mmol, 51%)) as a yellow solid.
$^1$H NMR (300 MHz, DMSO-$d_6$) δ: 11.69 (br. s., 1H), 9.20 (s, 1H), 9.09 (s, 1H), 8.34 (br. s., 2H), 7.84 (br. s., 3H), 7.68 (br. s., 1H), 7.37-7.46 (m, 1H), 7.26-7.35 (m, 1H), 4.15 (br. s., 2H), 3.90 (s, 3H), 3.17 (d, J=4.8 Hz, 2H); LCMS m/z [M+H]=482.

Example 13

2-(Azetindin-3-ylamino)-thieno[3,2-d]pyrimidine-7-carboxylic acid (1-methyl-1H-benzoimidazol-4-yl)-amide hydrochloride

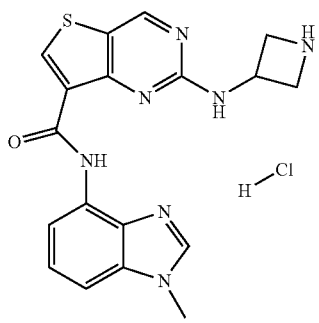 [SMILES: Cn1cnc2c(NC(=O)c3csc4cnc(NC5CNC5)nc34)cccc21 ; Cl]

Step 1

3-[7-(1-Methyl-1H-benzoimidazol-4-ylcarbamoyl)-thieno[3,2-d]pyrimidin-2-ylamino]-azetidine-1-carboxylic acid tert-butyl ester To a solution of 2-chloro-thieno[3,2-d]pyrimidine-7-carboxylic acid (1-methyl-1H-benzoimidazol-4-yl)-amide (0.043 g, 0.125 mmol) and 1-boc-3-(amino)azetindine (0.129 g, 0.750 mmol) in dioxane (3 mL) was added diisopropylethylamine (0.044 mL, 0.250 mmol). The reaction mixture was heated at 100° C. for 3 h. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 12 g, 50 to 90% ethyl acetate in hexanes) to give 3-[7-(1-methyl-1H-benzoimidazol-4-ylcarbamoyl)-thieno[3,2-d]pyrimidin-2-ylamino]-azetidine-1-carboxylic acid tert-butyl ester (0.039 g, 0.081 mmol, 65%) as a light yellow solid. LCMS m/z [M+H]=480.

Step 2

2-(Azetindin-3-ylamino)-thieno[3,2-d]pyrimidine-7-carboxylic acid (1-methyl-1H-benzoimidazol-4-yl)-amide hydrochloride A solution of 3-[7-(1-methyl-1H-benzoimidazol-4-ylcarbamoyl)-thieno[3,2-d]pyrimidin-2-ylamino]-azetidine-1-carboxylic acid tert-butyl ester (0.036 g, 0.075 mmol) in 4M HCl in dioxane (2 mL) was stirred at room temperature overnight. The mixture was concentrated in vacuo then the crude residue was washed with ether twice, concentrated and then dried to give 2-(Azetindin-3-ylamino)-thieno[3,2-d]pyrimidine-7-carboxylic acid (1-methyl-1H-benzoimidazol-4-yl)-amide hydrochloride (0.030 g, 0.072 mmol, 96%) as a yellow solid.
LCMS m/z [M+H]=380.

Example 14

2-(2-Methylamino-ethylamino)-thieno[3,2-d]pyrimidine-7-carboxylic acid (1-methyl-1H-benzoimidazol-4-yl)-amide hydrochloride

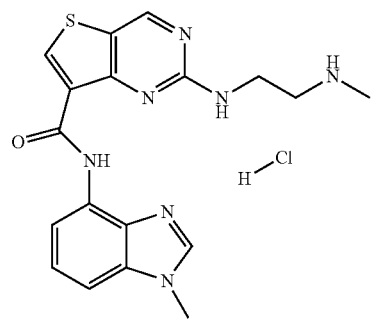 [SMILES: CNCCNc1ncc2scc(C(=O)Nc3cccc4c3ncn4C)c2n1 ; Cl]

Step 1

Methyl-{2-[7-(1-methyl-1H-benzoimidazol-4-ylcarbamoyl)-thieno[3,2-d]pyrimidin-2-ylamino]-ethyl}-carbamic acid tert-butyl ester To a solution of 2-chloro-thieno[3,2-d]pyrimidine-7-carboxylic acid (1-methyl-1H-benzoimidazol-4-yl)-amide (0.080 g, 0.233 mmol) and tert-butyl 2-aminoethyl(methyl)carbamate (0.0812 g, 0.466 mmol) in dioxane (3 mL) was added diisopropylethylamine (0.122 mL, 0.699 mmol). The reaction mixture was heated at 90° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 12 g, 50 to 90% ethyl acetate in hexanes) to give methyl-{2-[7-(1-methyl-1H-benzoimidazol-4-ylcarbamoyl)-thieno[3,2-d]pyrimidin-2-ylamino]-ethyl}-carbamic acid tert-butyl ester (0.034 g, 0.071 mmol, 30%) as a yellow sticky oil. LCMS m/z [M+H]=482.

Step 2

2-(2-Methylamino-ethylamino)-thieno[3,2-d]pyrimidine-7-carboxylic acid (1-methyl-1H-benzoimidazol-4-yl)-amide hydrochloride A solution of methyl-{2-[7-(1-methyl-1H-benzoimidazol-4-ylcarbamoyl)-thieno[3,2-d]pyrimidin-2-ylamino]-ethyl}- carbamic acid tert-butyl ester (0.031 g, 0.0644 mmol) in 4M HCl in dioxane (3 mL) was stirred at room temperature overnight. The mixture was concentrated in vacuo then the crude residue was washed with ether twice, concentrated and then dried in vacuo to give 2-(2-methylamino-ethylamino)-thieno[3,2-d]pyrimidine-7-carboxylic acid (1-methyl-1H-benzoimidazol-4-yl)-amide hydrochloride (0.028 g, 0.067 mmol, 104%) as a yellow solid.
LCMS m/z [M+H]=382.

Example 15

2-(cis-2-Amino-cyclohexylamino)-thieno[3,2-d]pyrimidine-7-carboxylic acid (6-fluoro-1-methyl-1H-indazol-3-yl)-amide trifluoroacetate

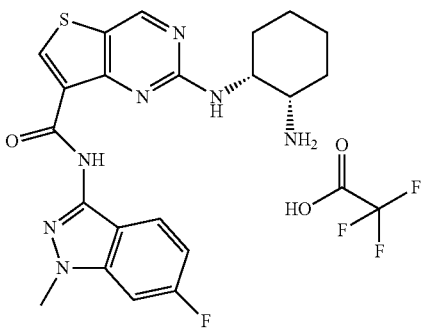

Step 1

2-Chloro-thieno[3,2-d]pyrimidine-7-carboxylic acid (6-fluoro-1-methyl-1H-indazol-3-yl)amide To a stirred solution of 2-chlorothieno[3,2-d]pyrimidine-7-carboxylic acid (0.050 g, 0.233 mmol) in DMF (2 mL) was added 6-fluoro-1-methyl-1H-indazol-3-amine (0.077 g, 0.466 mmol), DIPEA (0.0468 g, 0.362 mmol), and O-(benzotriazol-1-yl)-N,N,N',N'-bis-(tetramethylene)uranium hexafluoro-phosphate (0.043 g, 0.100 mmol). The reaction mixture was stirred at room temperature for 2 h. The reaction mixture was diluted with dichloromethane and water. The organic layer was washed with aqueous sodium carbonate, then brine, and then dried over anhydrous Na$_2$SO$_4$, and finally concentrated in vacuo. The residue was purified by chromatography (silica, 12 g, 40 to 80% ethyl acetate in hexanes) to give 2-chloro-thieno[3,2-d]pyrimidine-7-carboxylic acid (6-fluoro-1-methyl-1H-indazol-3-yl)amide (0.031 g, 0.086 mmol, 36.8%) as a light yellow semisolid. LCMS m/z [M+H]=362

Step 2

{cis-2-[7-(6-Fluoro-1-methyl-1H-indazol-3-ylcarbamoyl)-thieno[3,2-d]pyrimidin-2-ylamino]-cyclohexyl}-carbamic acid tert-butyl ester To a solution of 2-chloro-thieno[3,2-d]pyrimidine-7-carboxylic acid (6-fluoro-1-methyl-1H-indazol-3-yl)-amide (0.029 g, 0.080 mmol) and tert-butyl 2-aminocyclohexyl-carbamate (0.0344 g, 0.160 mmol) in dioxane (3 mL) was added diisopropylethylamine (0.042 mL, 0.240 mmol). The reaction mixture was heated at 90° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 12 g, 50 to 90% ethyl acetate in hexanes) to give {cis-2-[7-(6-fluoro-1-methyl-1H-indazol-3-ylcarbamoyl)-thieno[3,2-d]pyrimidin-2-ylamino]-cyclohexyl}-carbamic acid tert-butyl ester (0.017 g, 0.032 mmol, 39.3%) as a yellow sticky oil. LCMS m/z [M+H]=540.

Step 3

2-cis-2-Amino-cyclohexylamino)-thieno[3,2-d]pyrimidine-7-carboxylic acid (6-fluoro-1-methyl-1H-indazol-3-yl)-amide trifluoro-acetic acid To a solution of {cis-2-[7-(6-fluoro-1-methyl-1H-indazol-3-ylcarbamoyl)-thieno[3,2-d]pyrimidin-2-ylamino]-cyclohexyl}-carbamic acid tert-butyl ester (0.010 g, 0.0185 mmol) in dichloromethane (2 mL) was added TFA (0.400 mL, 5.19 mmol). The reaction mixture was stirred at room temperature overnight. The reaction mixture was concentrated in vacuo. The residue was washed twice with ether. The crude product was purified by preparative HPLC (10 to 80% acetonitrile in water with 0.05% TFA) to give 2-cis-2-amino-cyclohexylamino)-thieno[3,2-d]pyrimidine-7-carboxylic acid (6-fluoro-1-methyl-1H-indazol-3-yl)-amide trifluoro-acetic acid (0.002 g, 0.003 mmol, 15.5%) as a white solid.
$^1$H NMR (300 MHz, DMSO-d$_6$) δ: 11.48 (br. s., 1H), 9.22 (s, 1H), 9.03 (s, 1H), 7.79 (br. s., 3H), 7.68 (dd, J=8.7, 7.9 Hz, 1H), 7.44 (br. s., 1H), 6.89 (d, J=13.1 Hz, 1H), 6.79 (br. s., 1H), 4.37 (br. s., 2H), 3.38 (s, 3H), 1.55-1.85 (m, 6H), 1.42 (br. s., 2H). LCMS m/z [M+H]=440.

Example 16

2-((3R,4R))-3-amino-tetrahydro-pyran-4-ylamino)-thieno[3,2-d]pyrimidine-7-carboxylic acid naphthalene-2-ylamide

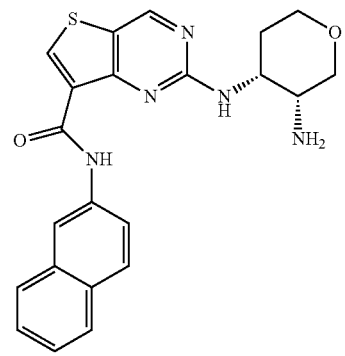 [SMILES: N[C@H]1COCC[C@H]1Nc1ncc2scc(C(=O)Nc3ccc4ccccc4c3)c2n1]

Step 1

2-Chloro-thieno[3,2-d]pyrimidine-7-carboxylic acid naphthlen-2-ylamide

To a stirred solution of 2-chlorothieno[3,2-d]pyrimidine-7-carboxylic acid (0.050 g, 0.233 mmol) in DMF (2 mL) was added naphthalene-2-amide (0.067 g, 0.466 mmol), DIPEA (0.163 mL, 0.932 mmol), 1-hydroxy-7-azabenzotriazole (0.048 g, 0.349 mmol) and HATU (0.133 g, 0.349 mmol). The reaction mixture was stirred at room temperature for 2 h. The reaction mixture was diluted with dichloromethane and water. The organic layer was washed with aqueous sodium carbonate, then brine, and then dried over anhydrous Na$_2$SO$_4$, filtered and concentrated in vacuo in vacuo. The residue was dried under high vacuum overnight to give 2-chloro-thieno[3,2-d]pyrimidine-7-carboxylic acid naphthlen-2-ylamide (0.105 g, 0.309 mmol, 133%) as a brown semi-solid, which was used directly in the next step without further purification. LCMS m/z [M+H]=340

Step 2

{(3R,4R)-4-[7-(Naphthalene-2-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid naphthalene-2-ylamide (0.0792 g, 0.233 mmol) and tert-butyl (3R,4R)-4-aminotetrahydro-2H-pyran-3-ylcarbamate (0.0756 g, 0.350 mmol) in dioxane (3 mL) was added diisopropylethylamine (0.122 mL, 0.699 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 60% ethyl acetate in hexanes) to give {(3R,4R)-4-[7-(naphthalene-2-ylcarbamoyl)-thieno[3,2-d]pyrimidin-2-ylamino]-tetrahydro-pyran-3-yl}-carbamic acid tert-butyl ester (0.063 g, 0.121 mmol, 52%) as a yellow solid. LCMS m/z [M+H]=520.

Step 3

2-((3R,4R))-3-Amino-tetrahydro-pyran-4-ylamino)-thieno[3,2-d]pyrimidine-7-carboxylic acid naphthalene-2-ylamide A solution of {(3R,4R)-4-[7-(naphthalene-2-ylcarbamoyl)-thieno[3,2-d]pyrimidin-2-ylamino]-tetrahydro-pyran-3-yl}-carbamic acid tert-butyl ester (0.063 g, 0.121 mmol) in 20% TFA in dichloromethane (2 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous Na$_2$SO$_4$, and concentrated in vacuo. The crude product was purified by chromatography (silica, 4 g, 0 to 10% MeOH in dichloromethane) to give 2-((3R,4R))-3-amino-tetrahydro-pyran-4-ylamino)-thieno[3,2-d]pyrimidine-7-carboxylic acid naphthalene-2-ylamide (0.027 g, 0.064 mmol, 53.1%) as a light yellow solid.

$^1$H NMR (300 MHz, DMSO-d$_6$) δ: 11.56 (s, 1H), 9.20 (s, 1H), 9.06 (s, 1H), 8.41 (br. s., 1H), 8.02 (d, J=8.8 Hz, 1H), 7.87-7.96 (m, 2H), 7.84 (br. s., 1H), 7.52-7.59 (m, 1H), 7.40-7.51 (m, 2H), 4.30 (br. s., 1H), 3.87 (br. s., 1H), 3.76 (d, J=8.3 Hz, 1H), 3.62 (dd, J=11.5, 2.0 Hz, 1H), 3.44-3.55 (m, 1H), 3.17 (br. s., 1H), 2.68 (s, 1H), 2.34 (s, 1H), 2.05-2.14 (m, 2H), 1.75-2.01 (m, 2H). LCMS m/z [M+H]=420

Example 17

2-((3R,4R))-3-Amino-tetrahydro-pyran-4-ylamino)-thieno[3,2-d]pyrimidine-7-carboxylic acid (5-methyl-pyridin-2-yl)-amide

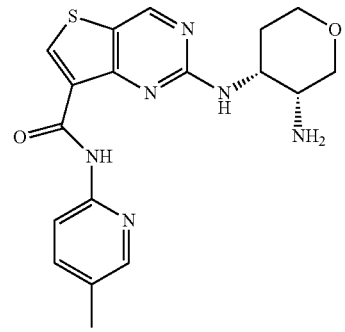 [SMILES: Cc1ccc(NC(=O)c2csc3cnc(N[C@@H]4CCOC[C@@H]4N)nc23)nc1]

Step 1

2-Chloro-thieno[3,2-d]pyrimidine-7-carboxylic acid (5-methyl-4,5-dihydro-pyridin-2-yl)-amide To a stirred solution of 2-chlorothieno[3,2-d]pyrimidine-7-carboxylic acid (0.050 g, 0.233 mmol) in DMF (2 mL) was added 5-methylpyridin-2-amine (0.0504 g, 0.466 mmol), DIPEA (0.163 mL, 0.932 mmol), 1-hydroxy-7-azabenzotriazole (0.048 g, 0.349 mmol) and HATU (0.133 g, 0.349 mmol). The reaction mixture was stirred at room temperature for 2 h. The reaction mixture was diluted with dichloromethane and water. The organic layer was washed with aqueous sodium carbonate, then brine, and then dried over anhydrous Na$_2$SO$_4$, filtered and concentrated in vacuo. The residue was dried under high vacuum overnight to give 2-chloro-thieno[3,2-d]pyrimidine-7-carboxylic acid (5-methyl-4,5-dihydro-pyridin-2-yl)-amide (0.097 g, 136%) as a brown semi-solid, which was used directly in the next step without further purification. LCMS m/z [M+H]=305.

Step 2

{(3R,4R)-4-[7-(5-Methyl-4,5-dihydro-pyridin-2-yl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid (5-methyl-4,5-dihydro-pyridin-2-yl)-amide (0.071 g, 0.233 mmol) and tert-butyl (3R,4R)-4-aminotetrahydro-2H-pyran-3-ylcarbamate (0.0756 g, 0.350 mmol) in dioxane (3 mL) was added diisopropylethylamine (0.122 mL, 0.699 mmol). The reaction mixture was heated at 120° C. overnight. The reaction mixture was cooled and then diluted with dichloromethane, washed with aqueous sodium carbonate, then brine, dried over anhydrous Na$_2$SO$_4$, filtered and concentrated. Purification by chromatography (silica, 40 g, 0 to 50% ethyl acetate in hexanes) gave {(3R,4R)-4-[7-(5-methyl-4,5-dihydro-pyridin-2-yl)-thieno[3,2-d]pyrimidin-2-ylamino]-tetrahydro-pyran-3-yl}-carbamic acid tert-butyl ester (0.047 g, 0.097 mmol, 41.6%) as a yellow solid. LCMS m/z [M+H]=485.

Step 3

2-((3R,4R))-3-Amino-tetrahydro-pyran-4-ylamino)-thieno[3,2-d]pyrimidine-7-carboxylic acid (5-methyl-pyridin-2-yl)-amide A solution of {(3R,4R)-4-[7-(5-methyl-4,5-dihydro-pyridin-2-yl)-thieno[3,2-d]pyrimidin-2-ylamino]-tetrahydro-pyran-3-yl}-carbamic acid tert-butyl ester (0.047 g, 0.97 mmol) in 20% TFA in dichloromethane (2 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous $Na_2SO_4$, and concentrated in vacuo. The crude product was purified by chromatography (silica, 4 g, 0 to 10% MeOH in dichloromethane) to give 2-((3R,4R))-3-amino-tetrahydro-pyran-4-ylamino)-thieno[3,2-d]pyrimidine-7-carboxylic acid (5-methyl-pyridin-2-yl)-amide (0.017 g, 0.044 mmol, 45.6%) as a light yellow solid.

$^1$H NMR (300 MHz, DMSO-$d_6$) δ: 12.09 (br. s., 1H), 9.16 (s, 1H), 9.04 (s, 1H), 8.08-8.37 (m, 2H), 7.69 (dd, J=8.4, 1.9 Hz, 1H), 7.31-7.52 (m, 1H), 4.19-4.47 (m, 1H), 3.89 (d, J=11.0 Hz, 1H), 3.77 (br. s., 2H), 3.60 (t, J=10.8 Hz, 1H), 3.16 (br. s., 1H), 2.67-2.99 (m, 2H), 2.29 (s, 3H), 1.66-2.01 (m, 2H). LCMS m/z [M+H]=385.

Example 18

2-((3R,4R))-3-Amino-tetrahydro-pyran-4-ylamino)-thieno[3,2-d]pyrimidine-7-carboxylic acid p-tolyl-amide

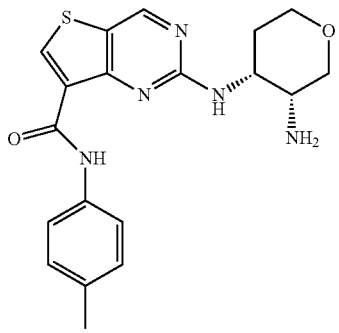

Step 1

2-Chloro-thieno[3,2-d]pyrimidine-7-carboxylic acid p-tolylamide

To a stirred solution of 2-chlorothieno[3,2-d]pyrimidine-7-carboxylic acid (0.075 g, 0.349 mmol) in DMF (3 mL) was added p-toluidine (0.075 g, 0.699 mmol), DIPEA (0.244 mL, 1.4 mmol), 1-hydroxy-7-azabenzotriazole (0.0713 g, 0.349 mmol) and HATU (0.199 g, 0.524 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid p-tolylamide (0.322 g) as a brown semi-solid, which was used directly in the next step without further purification. LCMS m/z [M+H]=304.

Step 2

{(3R,4R)-4-[7-(4-methyl-cyclohexa-1,5-dienylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid p-tolylamide (0.106 g, 0.349 mmol) and tert-butyl (3R,4R)-4-aminotetrahydro-2H-pyran-3-ylcarbamate (0.113 g, 0.524 mmol) in dioxane (4 mL) was added diisopropylethylamine (0.183 mL, 1.05 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 50% ethyl acetate in hexanes) to give {(3R,4R)-4-[7-(4-methyl-cyclohexa-1,5-dienylcarbamoyl)-thieno[3,2-d]pyrimidin-2-ylamino]-tetrahydro-pyran-3-yl}-carbamic acid tert-butyl ester (0.085 g) as a yellow solid. LCMS m/z [M+H]=484.

Step 3

2-((3R,4R))-3-Amino-tetrahydro-pyran-4-ylamino)-thieno[3,2-d]pyrimidine-7-carboxylic acid p-tolyl-amide A solution of {(3R,4R)-4-[7-(4-methyl-cyclohexa-1,5-dienylcarbamoyl)-thieno[3,2-d]pyrimidin-2-ylamino]-tetrahydro-pyran-3-yl}-carbamic acid tert-butyl ester (0.085 g, 0.176 mmol) in 20% TFA in dichloromethane (3 mL) was stirred at room temperature for 2 h. The reaction mixture was concentrated in vacuo. Dichloromethane and saturated sodium carbonate were added to the residue. The aqueous layer was washed with dichloromethane (3×). The organic layer was washed with brine, dried over anhydrous $Na_2SO_4$, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid p-tolylamide (0.036 g, 0.094 mmol, 53.4%) as a yellow solid.

$^1$H NMR (300 MHz, DMSO-$d_6$) δ: 11.31 (s, 1H), 9.17 (s, 1H), 8.99 (s, 1H), 7.66 (br. s., 2H), 7.39 (d, J=7.3 Hz, 1H), 7.25 (d, J=8.0 Hz, 2H), 4.19 (d, J=3.3 Hz, 1H), 3.84 (d, J=10.8 Hz, 1H), 3.72 (dd, J=11.3, 3.0 Hz, 1H), 3.52-3.62 (m, 1H), 3.39-3.49 (m, 2H), 3.06 (br. s., 1H), 2.32 (s, 3H), 1.91-2.01 (m, 2H). LCMS m/z [M+H]=384.

Example 19

2-((3R,4R))-3-Amino-tetrahydro-pyran-4-ylamino)-thieno[3,2-d]pyrimidine-7-carboxylic acid (1-methyl-1H-pyrazol-3-yl)-amide

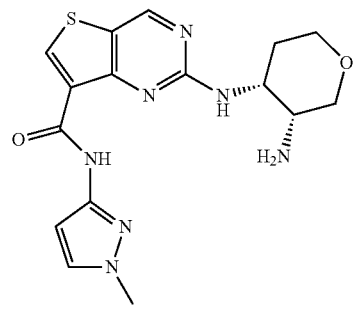 [SMILES: Cn1ccc(NC(=O)c2csc3cnc(N[C@@H]4CCOC[C@@H]4N)nc23)n1]

Step 1

2-Chloro-thieno[3,2-d]pyrimidine-7-carboxylic acid (1-methyl-1H-pyrazol-3-yl)-amide To a stirred solution of 2-chlorothieno[3,2-d]pyrimidine-7-carboxylic acid (0.075 g, 0.349 mmol) in DMF (3 mL) was added 1-methyl-1H-pyrazol-3-amine (0.051 g, 0.524 mmol), DIPEA (0.244 mL, 1.4 mmol), 1-hydroxy-7-azabenzotriazole (0.0713 g, 0.524 mmol) and HATU (0.199 g, 0.524 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid (1-methyl-1H-pyrazol-3-yl)-amide (0.123 g, 119%) as a brown solid, which was used directly in the next step without further purification. LCMS m/z [M+H]=294.

Step 2

{(3R,4R)-4-[7-(1-methyl-1H-pyrazol-3-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid (1-methyl-1H-pyrazol-3-yl)-amide (0.103 g, 0.349 mmol) and tert-butyl (3R,4R)-4-aminotetrahydro-2H-pyran-3-ylcarbamate (0.113 g, 0.524 mmol) in dioxane (4 mL) was added diisopropylethylamine (0.183 mL, 1.05 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% MeOH in dichloromethane) to give {(3R,4R)-4-[7-(1-methyl-1H-pyrazol-3-ylcarbamoyl)-thieno[3,2-d]pyrimidin-2-ylamino]-tetrahydro-pyran-3-yl}-carbamic acid tert-butyl ester (0.127 g, 0.268 mmol, 76.8%) as a yellow solid. LCMS m/z [M+H]=474.

Step 3

2-((3R,4R))-3-amino-tetrahydro-pyran-4-ylamino)-thieno[3,2-d]pyrimidine-7-carboxylic acid (1-methyl-1H-pyrazol-3-yl)-amide A solution of {(3R,4R)-4-[7-(1-methyl-1H-pyrazol-3-ylcarbamoyl)-thieno[3,2-d]pyrimidin-2-ylamino]-tetrahydro-pyran-3-yl}-carbamic acid tert-butyl ester (0.085 g, 0.176 mmol) in 20% TFA in dichloromethane (3 mL) was stirred at room temperature for 2 h. The reaction mixture was concentrated in vacuo. Dichloromethane and saturated sodium carbonate were added to the residue. The aqueous layer was washed with dichloromethane (3×). The organic layer was washed with brine, dried over anhydrous $Na_2SO_4$, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid (1-methyl-1H-pyrazol-3-yl)-amide (0.037 g, 0.099 mmol, 36.9%) as a yellow solid.

$^1$H NMR (300 MHz, DMSO-$d_6$) δ: 12.01 (br. s., 1H), 9.16 (s, 1H), 8.97 (s, 1H), 7.66 (d, J=2.0 Hz, 1H), 7.39 (br. s., 1H), 6.62 (d, J=2.3 Hz, 1H), 4.10-4.22 (m, 1H), 3.72-3.92 (m, 7H), 3.08 (br. s., 1H), 1.73-1.96 (m, 4H); LCMS m/z [M+H]=374.

Example 20

2-((3R,4R))-3-Amino-tetrahydro-pyran-4-ylamino)-thieno[3,2-d]pyrimidine-7-carboxylic acid thiazolo[4,5-b]pyridine-2-ylamide

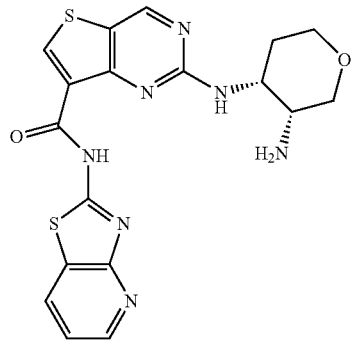 [SMILES: N[C@H]1COCC[C@H]1Nc1ncc2scc(C(=O)Nc3nc4ncccc4s3)c2n1]

Step 1

N-Thiazolo[4,5-c]pyridine-2-yl-benzamide

To a solution of ammonium thiocyanate (1.18 g, 15.6 mmol) in acetone (10 mL) was added benzoyl chloride (1.81 mL, 15.6 mmol) over 10 min. The reaction mixture was heated at 60° C. for 30 minutes, then 4-chloropyridin-3-amine (2.0 g, 15.6 mmol) in acetone (10 mL) was added over 10 min. The reaction mixture was heated at 60° C. for 2 h. Cold water (100 mL) was poured to the reaction mixture. The solid precipitate was filtered, washed with water, and dried under high vacuum to give N-thiazolo[4,5-c]pyridine-2-yl-benzamide (2.21 g, 8.66 mmol, 55.6%) as a light brown solid. This was used directly in the next step without further purification.

LCMS m/z [M+H]=256.

Step 2

Thiazolo[4,5-c]pyridine-2-ylamine

A solution of N-thiazolo[4,5-c]pyridine-2-yl-benzamide (2.21 g, 8.66 mmol) in sulfuric acid (12 mL) under nitrogen was stirred at 110° C. for 4 h. The reaction mixture was cooled down to 0° C., aqueous NaOH (50%) was added, the precipitated solid was filtered and washed with water, dried under high vacuum to give thiazolo[4,5-c]pyridine-2-ylamine (1.78 g, 136%) as a white solid. This was used directly in the next step without further purification. LCMS m/z [M+H]=152.

Step 3

2-Chloro-thieno[3,2-d]pyrimidine-7-carbonyl chloride

A solution of 2-chlorothieno[3,2-d]pyrimidine-7-carboxylic acid (0.100 g, 0.466 mmol) in thionyl chloride (3 mL) was refluxed for 4 h. The excess solvent was removed and then dried under high vacuum for 2 h to give 2-chloro-thieno[3,2-d]pyrimidine-7-carbonyl chloride (0.109 g, 0.466 mmol, 100%) as a yellow solid which was used directly in the next step without purification. LCMS m/z [M+H]=234

Step 4

2-Chloro-thieno[3,2-d]pyrimidine-7-carboxylic acid thiazol[4,5]b]pyrimidin-2-ylamide To a solution of 2-chloro-thieno[3,2-d]pyrimidine-7-carbonyl chloride (0.109 g, 0.466 mmol) in dichloromethane (4 mL) was added thiazolo[4,5-c]pyridine-2-ylamine (0.106 g, 0.699 mmol) and pyridine (0.113 mL, 1.4 mmol). The reaction mixture was stirred at room temperature overnight. The reaction mixture was diluted with EtOAc, washed with saturated sodium carbonate, then brine, dried over sodium sulfate, filtered, concentrated, and dried under high vacuum to give 2-chloro-thieno[3,2-d]pyrimidine-7-carboxylic acid thiazol[4,5]b]pyrimidin-2-ylamide (0.162 g, 0.466 mmol) which was used directly in the next step without further purification. LCMS m/z [M+H]=348

Step 5

{(3R,4R)-4-[7-(Thiazolo[4,5-b]pyridine-2-ylcarbamoyl)-thieno[3,2-d]pyrimidin-2-ylamino]-tetrahydro-pyran-3-yl}-carbamic acid tert-butyl ester To a solution of 2-chloro-N-(thiazolo[4,5-b]pyridin-2-yl)thieno[3,2-d]pyrimidine-7-carboxamide (0.162 g, 0.466 mmol) and tert-butyl (3R,4R)-4-aminotetrahydro-2H-pyran-3-ylcarbamate (0.151 g, 0.699 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% MeOH in dichloromethane) to give {(3R,4R)-4-[7-(thiazolo[4,5-b]pyridine-2-ylcarbamoyl)-thieno[3,2-d]pyrimidin-2-ylamino]-tetrahydro-pyran-3-yl}-carbamic acid tert-butyl ester (0.118 g, 0.224 mmol, 48%) as a yellow solid. LCMS m/z [M+H]=528.

Step 6

2-((3R,4R))-3-Amino-tetrahydro-pyran-4-ylamino)-thieno[3,2-d]pyrimidine-7-carboxylic acid thiazolo[4,5-b]pyridine-2-ylamide A solution of {(3R,4R)-4-[7-(thiazolo[4,5-b]pyridine-2-ylcarbamoyl)-thieno[3,2-d]pyrimidin-2-ylamino]-tetrahydro-pyran-3-yl}-carbamic acid tert-butyl ester (0.118 g, 0.224 mmol) in 20% TFA in dichloromethane (4 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous Na$_2$SO$_4$, and concentrated in vacuo. The crude product was purified by preparative HPLC (10 to 90% acetonitrile in water) to give 2-((3R,4R))-3-amino-tetrahydro-pyran-4-ylamino)-thieno[3,2-d]pyrimidine-7-carboxylic acid thiazolo[4,5-b]pyridine-2-ylamide (0.008 g, 0.019 mmol, 8%) as a yellow solid. LCMS m/z [M+H]=428.

Example 21

2-((3R,4R))-3-Amino-tetrahydro-pyran-4-ylamino)-thieno[3,2-d]pyrimidine-7-carboxylic acid (1-methyl-1H-pyrazol-4-yl)-amide

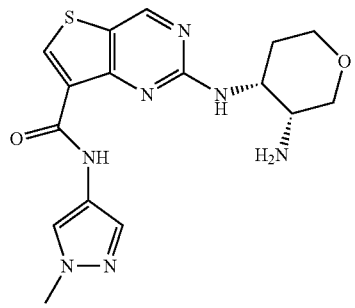 [SMILES: Cn1cc(NC(=O)c2csc3cnc(N[C@@H]4CCOC[C@@H]4N)nc23)cn1]

Step 1

2-Chloro-thieno[3,2-d]pyrimidine-7-carboxylic acid (1-methyl-1H-pyrazol-4-yl)-amide To a stirred solution of 2-chlorothieno[3,2-d]pyrimidine-7-carboxylic acid (0.100 g, 0.466 mmol) in DMF (4 mL) was added 1-methyl-1H-pyrazol-4-amine (0.068 g, 0.699 mmol), DIPEA (0.325 mL, 1.86 mmol), 1-hydroxy-7-azabenzotriazole (0.095 g, 0.699 mmol) and HATU (0.266 g, 0.699 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid (1-methyl-1H-pyrazol-4-yl)-amide (0.157 g, 115%) as a brown solid, which was used directly in the next step without further purification. LCMS m/z [M+H]=294.

Step 2

{(3R,4R)-4-[7-(1-Methyl-1H-pyrazol-4-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid (1-methyl-1H-pyrazol-4-yl)-amide (0.137 g, 0.349 mmol) and tert-butyl (3R,4R)-4-aminotetrahydro-2H-pyran-3-ylcarbamate (0.111 g, 0.513 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% MeOH in dichloromethane) to give {(3R,4R)-4-[7-(1-methyl-1H-pyrazol-4-ylcarbamoyl)-thieno[3,2-d]pyrimidin-2- ylamino]-tetrahydro-pyran-3-yl}-carbamic acid tert-butyl ester (0.116 g, 0.244 mmol, 52.6%) as a yellow solid. LCMS m/z [M+H]=474

Step 3

2-((3R,4R))-3-Amino-tetrahydro-pyran-4-ylamino)-thieno[3,2-d]pyrimidine-7-carboxylic acid (1-methyl-1H-pyrazol-4-yl)-amide A solution of {(3R,4R)-4-[7-(1-methyl-1H-pyrazol-4-ylcarbamoyl)-thieno[3,2-d]pyrimidin-2-ylamino]-tetrahydro-pyran-3-yl}-carbamic acid tert-butyl ester (0.116 g, 0.245 mmol) in 20% TFA in dichloromethane (3 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous Na$_2$SO$_4$, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid (1-methyl-1H-pyrazol-4-yl)-amide (0.034 g, 0.091 mmol, 37.2%) of as a yellow solid.

$^1$H NMR (300 MHz, DMSO-d$_6$) δ: 11.20 (br. s., 1H), 9.12-9.20 (m, 1H), 8.93 (s, 1H), 8.09 (br. s., 1H), 7.37 (d, J=7.3 Hz, 1H), 4.15 (br. s., 1H), 3.86 (s, 3H), 3.41-3.75 (m, 4H), 3.07 (d, J=2.3 Hz, 1H), 1.83-2.11 (m, 3H). LCMS m/z [M+H]=374.

Example 22

2-((3R,4R))-3-amino-tetrahydro-pyran-4-ylamino)-thieno[3,2-d]pyrimidine-7-carboxylic acid pyrazolo[1,5-a]pyrimidine-3-ylamide

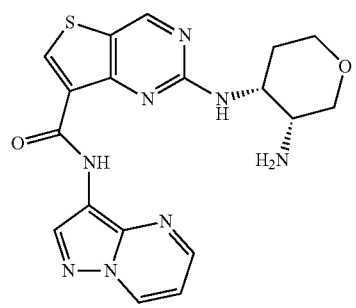 [SMILES: N[C@H]1COCC[C@H]1Nc1ncc2scc(C(=O)Nc3cnn4cccnc34)c2n1]

Step 1

2-Chloro-thieno[3,2-d]pyrimidine-7-carboxylic acid pyrazolo[1,5-a]pyrimidin-3-ylamide To a stirred solution of 2-chlorothieno[3,2-d]pyrimidine-7-carboxylic acid (0.100 g, 0.466 mmol) in DMF (4 mL) was added pyrazolo[1,5-a]pyrimidin-3-amine (0.094 g, 0.699 mmol), DIPEA (0.325 mL, 1.86 mmol), 1-hydroxy-7-azabenzotriazole (0.095 g, 0.699 mmol) and HATU (0.266 g, 0.699 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid pyrazolo[1,5-a]pyrimidin-3-ylamide (0.159 g, 103%) as a yellow solid, which was used directly in the next step without further purification. LCMS m/z [M+H]=331.

Step 2

{(3R,4R)-4-[7-(Pyrazolo[1,5-a]pyridine-3-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid pyrazolo[1,5-a]pyrimidin-3-ylamide (0.154 g, 0.466 mmol) and tert-butyl (3R,4R)-4-aminotetrahydro-2H-pyran-3-ylcarbamate (0.111 g, 0.513 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% MeOH in dichloromethane) to give {(3R,4R)-4-[7-(pyrazolo[1,5-a]pyridine-3-ylcarbamoyl)-thieno[3,2-d]pyrimidin-2-ylamino]-tetrahydro-pyran-3-yl}-carbamic acid tert-butyl ester (0.137 g, 0.268 mmol, 57%) as a yellow solid. LCMS m/z [M+H]=511.

Step 3

2-((3R,4R))-3-amino-tetrahydro-pyran-4-ylamino)-thieno[3,2-d]pyrimidine-7-carboxylic acid pyrazolo[1,5-a]pyrimidine-3-ylamide A solution of {(3R,4R)-4-[7-(pyrazolo[1,5-a]pyridine-3-ylcarbamoyl)-thieno[3,2-d]pyrimidin-2-ylamino]-tetrahydro-pyran-3-yl}-carbamic acid tert-butyl ester (0.137 g, 0.268 mmol) in 20% TFA in dichloromethane (4 mL) was stirred at room temperature for 1 h. The reaction mixture was concentrated in vacuo. Dichloromethane and saturated sodium carbonate were added to the residue. The aqueous layer was washed with dichloromethane (3×). The organic layers were combined and washed with brine, dried over anhydrous Na$_2$SO$_4$, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid pyrazolo[1,5-a]pyrimidine-3-ylamide (0.055 g, 134 mmol, 50%) as a yellow solid.

$^1$H NMR (300 MHz, DMSO-d$_6$) δ: 11.57 (br. s., 1H), 9.16 (s, 1H), 9.12 (dd, J=7.2, 1.4 Hz, 1H), 9.01 (s, 1H), 8.82 (br. s., 1H), 8.58 (dd, J=3.9, 1.4 Hz, 1H), 7.33 (br. s., 1H), 7.10 (dd, J=7.0, 4.0 Hz, 1H), 3.48-3.78 (m, 4H), 3.06 (br. s., 1H), 1.91 (d, J=8.3 Hz, 2H). LCMS m/z [M+H]=411.

Example 23

2-((3R,4R))-3-Amino-tetrahydro-pyran-4-ylamino)-thieno[3,2-d]pyrimidine-7-carboxylic acid imidazol[1,2-b]pyridazine-3-ylamide

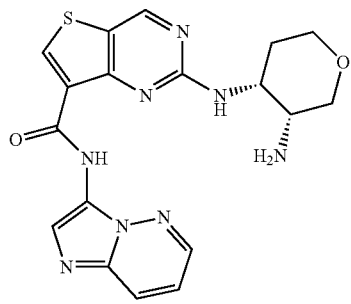 [SMILES: N[C@H]1COCC[C@H]1Nc1ncc2scc(C(=O)Nc3cnc4cccnn34)c2n1]

Step 1

2-Chloro-thieno[3,2-d]pyrimidine-7-carboxylic acid imidazol[1,2-b]pyridazin-3-ylamide To a stirred solution of 2-chlorothieno[3,2-d]pyrimidine-7-carboxylic acid (0.100 g, 0.466 mmol) in DMF (4 mL) was added imidazol[1,2-b]pyridazin-3-amine (0.094 g, 0.699 mmol), DIPEA (0.325 mL, 1.86 mmol), 1-hydroxy-7-azabenzotriazole (0.095 g, 0.699 mmol) and HATU (0.266 g, 0.699 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid imidazol[1,2-b]pyridazin-3-ylamide (0.171 g, 111%) as a yellow solid, which was used directly in the next step without further purification. LCMS m/z [M+H]=331.

Step 2

{(3R,4R)-4-[7-(Imidazole[1,2-b]pyridazin-3-ylcarbamoyl)-thieno[3,2-d]pyrimidin-2-ylamino]-tetrahydro-pyran-3-yl}-carbamic acid tert-butyl ester To a solution of 2-chloro-thieno[3,2-d]pyrimidine-7-carboxylic acid imidazol[1,2-b]pyridazin-3-ylamide (0.154 g, 0.466 mmol) and of tert-butyl (3R,4R)-4-aminotetrahydro-2H-pyran-3-ylcarbamate (0.121 g, 0.559 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% MeOH in dichloromethane) to give {(3R,4R)-4-[7-(imidazole[1,2-b]pyridazin-3-ylcarbamoyl)-thieno[3,2-d]pyrimidin-2-ylamino]-tetrahydro-pyran-3-yl}-carbamic acid tert-butyl ester (0.163 g, 0.319 mmol, 68.5%) as a yellow solid. LCMS m/z [M+H]=511.

Step 3

2-((3R,4R))-3-Amino-tetrahydro-pyran-4-ylamino)-thieno[3,2-d]pyrimidine-7-carboxylic acid imidazol[1,2-b]pyridazine-3-ylamide A solution of {(3R,4R)-4-[7-(imidazole[1,2-b]pyridazin-3-ylcarbamoyl)-thieno[3,2-d]pyrimidin-2-ylamino]-tetrahydro-pyran-3-yl}-carbamic acid tert-butyl ester (0.163 g, 0.319 mmol) in 20% TFA in dichloromethane (4 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous $Na_2SO_4$, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid imidazol[1,2-b]pyridazine-3-ylamide (0.030 g, 0.073 mmol, 22.9%) as a yellow solid. LCMS m/z [M+H]=411. $^1$H NMR (300 MHz, DMSO-$d_6$) δ: 9.20 (s, 1H), 9.09 (s, 1H), 8.69 (d, J=3.5 Hz, 1H), 8.19 (d, J=9.3 Hz, 1H), 8.11 (br. s., 1H), 7.26 (dd, J=9.2, 4.4 Hz, 1H), 4.59 (br. s., 1H), 3.57-3.77 (m, 4H), 3.06 (br. s., 1H), 1.80 (d, J=4.3 Hz, 3H).

Example 24

2-((3R,4R))-3-Amino-tetrahydro-pyran-4-ylamino)-thieno[3,2-d]pyrimidine-7-carboxylic acid (4,6-dimethyl-pyridin-2-yl)-amide

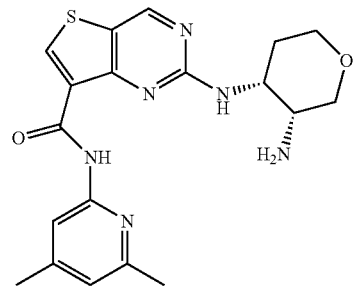 [SMILES: Cc1cc(C)nc(NC(=O)c2csc3cnc(N[C@@H]4CCOC[C@@H]4N)nc23)c1]

Step 1

2-Chloro-thieno[3,2-d]pyrimidine-7-carboxylic acid (4,6-dimethyl-pyridin-2-yl)-amide To a stirred solution of 2-chlorothieno[3,2-d]pyrimidine-7-carboxylic acid (0.100 g, 0.466 mmol) in DMF (4 mL) was added 4,6-dimethylpyridin-2-amine (0.085 g, 0.699 mmol), DIPEA (0.325 mL, 1.86 mmol), 1-hydroxy-7-azabenzotriazole (0.095 g, 0.699 mmol) and HATU (0.266 g, 0.699 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid (4,6-dimethyl-pyridin-2-yl)-amide (0.222 g, 149%) as a yellow solid, which was used directly in the next step without further purification. LCMS m/z [M+H]=319.

Step 2

{(3R,4R)-4-[7-(4,6-Dimethyl-pyridin-2-ylcarbamoyl)-thieno[3,2-d]pyrimidin-2-ylamino]-tetrahydropyran-3-yl}-carbamic acid tert-butyl ester To a solution of 2-chloro-thieno[3,2-d]pyrimidine-7-carboxylic acid (4,6-dimethyl-pyridin-2-yl)-amide (0.149 g, 0.466 mmol) and tert-butyl (3R,4R)-4-aminotetrahydro-2H-pyran-3-ylcarbamate (0.121 g, 0.559 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% EtOAc in hexanes) to give {(3R,4R)-4-[7-(4,6-dimethyl-pyridin-2-ylcarbamoyl)-thieno[3,2-d]pyrimidin-2-ylamino]-tetrahydropyran-3-yl}-carbamic acid tert-butyl ester (0.104 g, 0.209 mmol, 44.8%) as a yellow solid. LCMS m/z [M+H]=499.

Step 3

2-((3R,4R))-3-Amino-tetrahydro-pyran-4-ylamino)-thieno[3,2-d]pyrimidine-7-carboxylic acid (4,6-dimethyl-pyridin-2-yl)-amide A solution of {(3R,4R)-4-[7-(4,6-dimethyl-pyridin-2-ylcarbamoyl)-thieno[3,2-d]pyrimidin-2-ylamino]-tetrahydropyran-3-yl}-carbamic acid tert-butyl ester (0.102 g, 0.205 mmol) in 20% TFA in dichloromethane (4 mL) was stirred at room temperature for 1 h. The reaction mixture was concentrated in vacuo. Dichloromethane and saturated sodium carbonate were added to the residue. The aqueous layer was washed with dichloromethane (3×). The organic layer was washed with brine, dried over anhydrous Na₂SO₄, and concentrated in vacuo. The crude product was purified by chromatography (silica, 4 g, 0 to 15% MeOH in dichloromethane) to give 2-((3R,4R))-3-amino-tetrahydro-pyran-4-ylamino)-thieno[3,2-d]pyrimidine-7-carboxylic acid (4,6-dimethyl-pyridin-2-yl)-amide (0.045 g, 0.113 mmol, 55.2%) as a yellow solid.

$^1$H NMR (300 MHz, DMSO-$d_6$) δ: 11.76 (br. s., 1H), 9.15 (s, 1H), 9.02 (s, 1H), 8.00 (s, 1H), 7.38 (br. s., 1H), 6.89 (s, 1H), 4.34 (br. s., 1H), 3.58-3.85 (m, 4H), 3.04 (br. s., 1H), 2.45 (s, 3H), 2.33 (s, 3H), 1.69-1.93 (m, 4H). LCMS m/z [M+H]=399.

Example 25

2-((3R,4R))-3-Amino-tetrahydro-pyran-4-ylamino)-thieno[3,2-d]pyrimidine-7-carboxylic acid (5,6-dimethyl-pyridin-2-yl)-amide

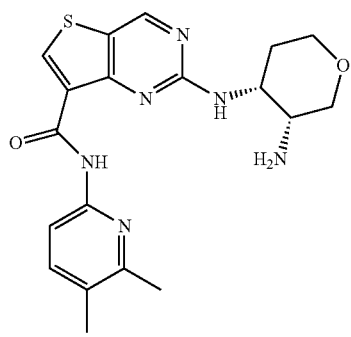 [SMILES: Cc1ccc(NC(=O)c2csc3cnc(N[C@@H]4CCOC[C@@H]4N)nc23)nc1C]

Step 1

2-Chloro-thieno[3,2-d]pyrimidine-7-carboxylic acid (5,6-dimethyl-pyridin-2-yl)-amide To a stirred solution of 2-chlorothieno[3,2-d]pyrimidine-7-carboxylic acid (0.100 g, 0.466 mmol) in DMF (4 mL) was added 5,6-dimethylpyridin-2-amine (0.085 g, 0.699 mmol), DIPEA (0.325 mL, 1.86 mmol), 1-hydroxy-7-azabenzotriazole (0.095 g, 0.699 mmol) and HATU (0.266 g, 0.699 mmol). The reaction mixture was stirred at room temperature for 2 h. The reaction mixture was diluted with dichloromethane and water. The organic layer was washed with aqueous sodium carbonate, then brine, and then dried over anhydrous sodium sulfate, filtered and concentrated in vacuo. The residue was dried under high vacuum overnight to give 2-chloro-thieno[3,2-d]pyrimidine-7-carboxylic acid (5,6-dimethyl-pyridin-2-yl)-amide as a yellow solid, which was used directly in the next step without further purification. LCMS m/z [M+H]=319.

Step 2

{(3R,4R)-4-[7-(5,6-Dimethyl-pyridin-2-ylcarbamoyl)-thieno[3,2-d]pyrimidin-2-ylamino]-tetrahydropyran-3-yl}-carbamic acid tert-butyl ester To a solution of 2-chloro-thieno[3,2-d]pyrimidine-7-carboxylic acid (5,6-dimethyl-pyridin-2-yl)-amide (0.149 g, 0.466 mmol) and tert-butyl (3R,4R)-4-aminotetrahydro-2H-pyran-3-ylcarbamate (0.121 g, 0.559 mmol) in dioxane (4 mL) was added diisopropylethylamine (0.244 mL, 1.4 mmol). The reaction mixture was heated at 120° C. overnight. The reaction mixture was cooled and then diluted with dichloromethane, washed with aqueous sodium carbonate, then brine, dried over anhydrous sodium sulfate, filtered and concentrated in vacuo. The residue obtained was then purified by chromatography (silica, 40 g, 0 to 15% EtOAc in hexanes) to give {(3R,4R)-4-[7-(5,6-dimethyl-pyridin-2-ylcarbamoyl)-thieno[3,2-d]pyrimidin-2-ylamino]-tetrahydropyran-3-yl}-carbamic acid tert-butyl ester (0.105 g, 0.210 mmol, 45%) as a yellow solid. LCMS m/z [M+H]=499.

Step 3

2-((3R,4R))-3-Amino-tetrahydro-pyran-4-ylamino)-thieno[3,2-d]pyrimidine-7-carboxylic acid (5,6-dimethyl-pyridin-2-yl)-amide A solution of {(3R,4R)-4-[7-(5,6-dimethyl-pyridin-2-ylcarbamoyl)-thieno[3,2-d]pyrimidin-2-ylamino]-tetrahydropyran-3-yl}-carbamic acid tert-butyl ester (0.102 g, 205 mmol) in 20% TFA in dichloromethane (4 mL) was stirred at room temperature for 1 h. The reaction mixture was concentrated in vacuo. Dichloromethane and saturated sodium carbonate were added to the residue. The aqueous layer was washed with dichloromethane (3×). The combined organic phases were washed with brine, dried over anhydrous Na₂SO₄, and concentrated in vacuo. The crude product was purified by chromatography (silica, 4 g, 0 to 10% MeOH in dichloromethane) to give 2-((3R,4R))-3-amino-tetrahydro-pyran-4-ylamino)-thieno[3,2-d]pyrimidine-7-carboxylic acid (5,6-dimethyl-pyridin-2-yl)-amide (0.041 g, 0.103 mmol, 50.3%) as a yellow solid.

$^1$H NMR (300 MHz, DMSO-$d_6$) δ: 11.73 (br. s., 1H), 9.15 (s, 1H), 9.02 (s, 1H), 8.05 (d, J=8.0 Hz, 1H), 7.59 (d, J=8.3 Hz, 1H), 7.38 (br. s., 1H), 4.35 (br. s., 1H), 3.54-3.87 (m,

4H), 3.06 (br. s., 1H), 2.44 (s, 3H), 2.24 (s, 3H), 1.71-1.93 (m, 2H). LCMS m/z [M+H]=399.

BIOLOGICAL EXAMPLES

SYK Assay Information

Determination of $IC_{50}$ of Spleen Tyrosine Kinase (SYK) inhibition: SYK kinase assay is a standard kinase assay adapted to a 96 well plate format. This assay is performed in 96-well format for $IC_{50}$ determination with 8 samples which represented 10 half log dilutions and a 40 µL reaction volume. The assay measures the incorporation of radiolabeled $^{33}$P gATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)
Streptavidin coated beads: Streptavidin Sepharose™, suspension 5.0 mL, in 50 mM EDTA/PBS diluted (1:100), (Amersham, Cat. No.: 17-5113-01)
Compounds: 10 mM in 100% dimethylsulfoxide (DMSO), final conc.: compound 0.003-100 uM in 10% DMSO
Enzyme: Recombinant human full length SYK protein (Invitrogen Cat. No.: PV4089) dephosphotylated by protein tyrosine phosphatase PTP1B, working solution 8.89 nM, final conc.: 0.004 µM.
Peptide 1: biotinylated peptide is derived from a naturally occurring phosphor-acceptor con-sensus sequence (Biotin-EPEGDYEEVLE), special order from QCB, stock solution 20 mM, final conc.: 10 µM.
ATP: Adenosine-5'-triphosphate 20 mM, (ROCHE Cat. No.: 93202720), final concentration: 20 µM
Buffer: HEPES: 2-Hydroxyethyl piperazine-2-ethanesulfonic acid (Sigma, Cat. No.: H-3375)
final concentration: 50 mM HEPES pH7.5
BSA: Bovine Serum Albumin Fraction V, fatty acid free (Roche Diagnostics GmbH, Cat. No. 9100221) diluted to a final concentration of 0.1%
EDTA: EDTA stock solution 500 mM, (GIBCO, Cat. No.: 15575-038) final concentration: 0.1 mM
DTT: 1,4-Dithiothreitol (Roche Diagnostics GmbH, Cat. No.: 197777), final conc.: 1 mM
$MgCl_2 \times 6H_2O$: MERCK, Cat. No.: 105833.1000, final concentration: 10 mM
Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5
Bead wash buffer: 10 g/L PBS (Phosphate buffered saline) with 2M NaCl+1% phosphoric acid.
Experimental Method:

In 20 µL volume, 18 µL of recombinant human full length SYK [8.89 nM] was mixed with 2 µL of 10× concentrations of the test compounds, [usually 100 µM-0.003 µM] in [10%] DMSO and the mixture was incubated for 15 min at RT.

The kinase reaction was initiated by the addition of 20 µL 2× substrate cocktail containing the Biotin-peptide substrate [20 µM], ATP [40 µM] and $^{33}$PγATP [2 µCi/rxn]. After incubation at RT for 30 min, the reaction was terminated by the transfer of 25 µL of the reaction sample to a 96 well 0.65 µm Millipore MADVNOB membrane/plate containing 100 µL 5 mM EDTA and 10% Streptavidine coated beads in PBS.

The unbound radionucleotides were washed under vacuum with 3×250 µL 2M NaCl; 2×250 µL 2M NaCl+1% phosphoric acid and 1×250 µL $H_2O$. After the last wash, membrane/plates were transferred to an adaptor plate, heat dried for 1 hour min at 60° C., and 60 µL scintillation cocktail was added to each well and the amount of radioactivity was counted in a top counter.

The percent inhibition was calculated based on the uninhibited enzyme rate: % Inhibition=(1−((Test−Positive Control)/(Negative Control−Positive Control)))*100 The $IC_{50}$ was calculated using a non-linear curve fit with XLfit software (ID Business Solution Ltd., Guilford, Surrey, UK).

B Cell CD69 Up-Regulation Assay in Human Whole Blood

Human Blood was collected from healthy volunteers into Vacutainers (BD Biosciences, San Jose, Calif.) containing sodium heparin. Test compound was suspended in DMSO and nine half-log serial dilutions were made. The concentration of DMSO in the assay was 0.5%. 100 mL whole blood was pre-incubated with compound for 30 min and then stimulated with goat anti-human IgM (50 µg/ml, Southern Biotech) for 20 hrs. At the end of the 20 hour incubation, samples were incubated with fluorochrome-conjugated antibodies, PE mouse anti-human CD20 and APC Mouse anti-human CD69 (BD Biosciences), for 30 minutes. Samples were then lysed with Lyse solution (BD) and washed with PBS containing 2% fetal bovine serum (FBS). Fluorescent signals were acquired on flow cytometer LSR II (BD) and data were analyzed by Flow Jo. The percentage of activated (CD69hi) B-cell lymphocytes (CD20+) were determined using un-stimulated (negative control) and stimulated (positive control) wells as reference guidelines. The percentage inhibition was calculated and an IC50 curve was constructed using Xfit in Microsoft Excel with sigmoidal curve fitting. Representative data shown in Table below:

| Compound | Syk, IC50 uM | HWB, IC50, uM |
|---|---|---|
| 1 | 0.139 | 5.38 |
| 2 | <0.001 | 0.19 |
| 3 | 0.004 | 0.76 |
| 4 | 0.041 | 50.00 |
| 5 | 0.079 | 3.79 |
| 6 | 0.143 | 4.29 |
| 7 | 0.011 | 0.55 |
| 8 | 0.225 | 50.00 |
| 9 | 0.041 | 50.00 |
| 10 | 0.122 | 3.74 |
| 11 | 0.615 | 1.44 |
| 12 | 0.435 | 3.06 |
| 13 | 10.000 | |
| 14 | 2.462 | |
| 15 | 5.977 | 50.00 |
| 16 | 0.006 | 3.73 |
| 17 | 0.146 | |
| 18 | 0.413 | 12.15 |
| 19 | 0.852 | 10.69 |
| 20 | 0.280 | |
| 21 | 1.106 | 5.80 |
| 22 | 0.238 | 0.92 |
| 23 | 0.560 | 1.36 |
| 24 | 0.058 | 1.53 |
| 25 | 0.168 | 1.67 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

We claim:
1. A compound of Formula I

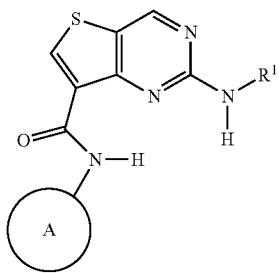

wherein:
each A is independently monocyclic or bicyclic aryl, pyridyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole, oxadiaxoline, isoquinolinyl, benzofuryl, benzothiophenyl, benzoxazole, benzisoxazole, benzothiazole, naphthyridinyl, 5,6,7,8-Tetrahydro-[1,6]naphthyridinyl or benzisothiazole, optionally substituted with one or more A' or
A is quinolinyl substituted with one or more A';
each A' is independently lower alkyl, halo, cyano, or heteroaryl; and
$R^1$ is tetrahydropyranyl substituted with amino,
or a pharmaceutically acceptable salt thereof.
2. The compound of claim 1, wherein A is pyridyl, optionally substituted with one or more A'.
3. A compound selected from the group consisting of:
2-((3R,4R)-3-Amino-tetrahydro-pyran-4-ylamino)-thieno[3,2-d]pyrimidine-7-carboxylic acid (6-[1,2,3]triazol-2-yl-pyridin-2-yl)-amide;
2-((3R,4R)-3-Amino-tetrahydro-pyran-4-ylamino)-thieno[3,2-d]pyrimidine-7-carboxylic acid (6-[1,2,3]triazol-1-yl-pyridin-2-yl)-amide;
2-((3R,4R)-3-Amino-tetrahydro-pyran-4-ylamino)-thieno [3,2-d]pyrimidine-7-carboxylic acid (1-methyl-1H-benzoimidazol-4-yl)-amide hydrochloride;
2-((3R,4R)-3-Amino-tetrahydro-pyran-4-ylamino)-thieno[3,2-d]pyrimidine-7-carboxylic acid naphthalen-2-ylamide;
2-((3R,4R)-3-Amino-tetrahydro-pyran-4-ylamino)-thieno[3,2-d]pyrimidine-7-carboxylic acid (5-methyl-pyridin-2-yl)-amide;
2-((3R,4R)-3-Amino-tetrahydro-pyran-4-ylamino)-thieno[3,2-d]pyrimidine-7-carboxylic acid p-tolylamide;
2-((3R,4R)-3-Amino-tetrahydro-pyran-4-ylamino)-thieno[3,2-d]pyrimidine-7-carboxylic acid (1-methyl-1H-pyrazol-3-yl)-amide;
2-((3R,4R)-3-Amino-tetrahydro-pyran-4-ylamino)-thieno [3,2-d]pyrimidine-7-carboxylic acid thiazolo[4,5-b]pyridin-2-ylamide;
2-((3R,4R)-3-Amino-tetrahydro-pyran-4-ylamino)-thieno[3,2-d]pyrimidine-7-carboxylic acid (1-methyl-1H-pyrazol-4-yl)-amide;
2-((3R,4R)-3-Amino-tetrahydro-pyran-4-ylamino)-thieno [3,2-d]pyrimidine-7-carboxylic acid pyrazolo[1,5-a]pyrimidin-3-ylamide;
2-((3R,4R)-3-Amino-tetrahydro-pyran-4-ylamino)-thieno[3,2-d]pyrimidine-7-carboxylic acid imidazo[1,2-b]pyridazin-3-ylamide;
2-((3R,4R)-3-Amino-tetrahydro-pyran-4-ylamino)-thieno[3,2-d]pyrimidine-7-carboxylic acid (4,6-dimethyl-pyridin-2-yl)-amide; and
2-((3R,4R)-3-Amino-tetrahydro-pyran-4-ylamino)-thieno[3,2-d]pyrimidine-7-carboxylic acid (5,6-dimethyl-pyridin-2-yl)-amide,
or a pharmaceutically acceptable salt thereof.
4. A method for treating rheumatoid arthritis comprising administering to a patient in need thereof a therapeutically effective amount of the compound of claim 1.
5. A pharmaceutical composition, comprising a therapeutically effective amount of a compound of claim 1, or a pharmaceutically acceptable salt thereof, admixed with at least one pharmaceutically acceptable carrier, excipient or diluent.
6. The pharmaceutical composition of claim 5, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

* * * * *

UNITED STATES PATENT AND TRADEMARK OFFICE
CERTIFICATE OF CORRECTION

PATENT NO. : 9,701,691 B2  
APPLICATION NO. : 13/738103  
DATED : July 11, 2017  
INVENTOR(S) : Shaoqing Chen et al.

It is certified that error appears in the above-identified patent and that said Letters Patent is hereby corrected as shown below:

On the Title Page

(73) Assignee should read as follows:  
--Hoffmann-La Roche Inc., Nutley, NJ (US)--

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*